US012580106B2

(12) United States Patent (10) Patent No.: US 12,580,106 B2
Aas et al. (45) Date of Patent: Mar. 17, 2026

(54) PROCESS FOR PREPARATION OF SILICA COATED MAGNETIC PARTICLES

(71) Applicant: NORWEGIAN UNIVERSITY OF SCIENCE AND TECHNOLOGY, Trondheim (NO)

(72) Inventors: Per Arne Aas, Trondheim (NO); Lars Hagen, Trondheim (NO); Sten Even Erlandsen, Trondheim (NO); Magnar Bjørås, Trondheim (NO); Vegar Ottesen, Trondheim (NO); Anuvansh Sharma, Trondheim (NO); Sulalit Bandyopadhyay, Trondheim (NO)

(73) Assignee: NORWEIGAN UNIVERSITY OF SCIENCE AND TECHNOLOGY, Trondheim (NO)

( * ) Notice: Subject to any disclaimer, the term of this patent is extended or adjusted under 35 U.S.C. 154(b) by 499 days.

(21) Appl. No.: 17/916,168

(22) PCT Filed: Apr. 1, 2021

(86) PCT No.: PCT/EP2021/058780
§ 371 (c)(1),
(2) Date: Sep. 30, 2022

(87) PCT Pub. No.: WO2021/198502
PCT Pub. Date: Oct. 7, 2021

(65) Prior Publication Data
US 2023/0223175 A1      Jul. 13, 2023

(30) Foreign Application Priority Data

Apr. 3, 2020    (GB) ..................................... 2004987
Apr. 3, 2020    (GB) ..................................... 2004988
(Continued)

(51) Int. Cl.
*H01F 41/16*      (2006.01)
*B22F 1/16*       (2022.01)
(Continued)

(52) U.S. Cl.
CPC .............. *H01F 1/0054* (2013.01); *B22F 1/16* (2022.01); *G01N 33/54326* (2013.01); *H01F 1/015* (2013.01); *H01F 41/16* (2013.01)

(58) Field of Classification Search
None
See application file for complete search history.

(56) References Cited

U.S. PATENT DOCUMENTS 8,323,899  B2    12/2012  Sherman et al.
2007/0015165 A1    1/2007  Chen et al.
(Continued)

FOREIGN PATENT DOCUMENTS

CN        106591297  A     4/2017
CN        108853521  A     11/2018
(Continued)

OTHER PUBLICATIONS

Ligang Gai et al., "Preparation of core-shell Fe3O4/SiO2 microspheres as adsorbents for purification of DNA", Journal of Physics D: Applied Physics 2010, vol. 43, 445001.1-445001.8.
(Continued)

*Primary Examiner* — George Wyszomierski
(74) *Attorney, Agent, or Firm* — Meunier Carlin & Curfman LLC

(57)                    ABSTRACT
The present invention relates to methods and products for isolating nucleic acids from samples containing biological material. In particular, the present invention relates to silica-coated magnetic particles, processes for their preparation and their use in methods of isolating nucleic acids samples containing biological material.

12 Claims, 1 Drawing Sheet

(30) Foreign Application Priority Data

| | | |
|---|---|---|
| Apr. 3, 2020 | (NO) | ..................................... 20200427 |
| Apr. 3, 2020 | (NO) | ..................................... 20200428 |
| Jul. 9, 2020 | (GB) | ..................................... 2010567 |
| Jul. 9, 2020 | (GB) | ..................................... 2010570 |

(51) Int. Cl.

| | |
|---|---|
| *G01N 33/543* | (2006.01) |
| *H01F 1/00* | (2006.01) |
| *H01F 1/01* | (2006.01) |

(56) References Cited

U.S. PATENT DOCUMENTS

| | | | |
|---|---|---|---|
| 2011/0274832 A1* | 11/2011 | Dai ....................... | H01F 1/0054 |
| | | | 427/127 |
| 2013/0260369 A1 | 10/2013 | Fischer et al. | |
| 2016/0348153 A1 | 12/2016 | Narayanan et al. | |
| 2017/0327815 A1 | 11/2017 | Will | |
| 2018/0201977 A1 | 7/2018 | Gaeta | |
| 2020/0265979 A1* | 8/2020 | Hug ................... | H01F 41/0206 |

FOREIGN PATENT DOCUMENTS

| | | | |
|---|---|---|---|
| EP | 2388312 A1 | 11/2011 | |
| WO | 2001071732 A2 | 9/2001 | |
| WO | 2014090838 A1 | 6/2014 | |
| WO | 2018/223067 A1 | 12/2018 | |

OTHER PUBLICATIONS

Zeinab Sharafi et al., "Synthesis of silica-coated iron oxide nanoparticles: preventing aggregation without using additives or seed pretreatment", Iran J Pharm Res. 2018; 17(1): 386-395.

S. Berensmeier, "Magnetic particles for separation and purification of nucleic acids", Appl Microbiol. Biotetechnol. 2006; 73(3): 495-504.

G. H. Bogush et al., "Preparation of monodisperse silica particles: Control of size and mass fraction", Journal of Non-Crystalline Solids, vol. 104, Issue 1, Aug. 1988, pp. 95-106.

Ki Wan Jang et al., "The effects of the water content, acidity, temperature and alcohol content on the acidic sol-gel polymerisation of tetraethoxysilane (TEPOS) with Monte Carlo Simulation" Simulation vol. 27, 2001—issue 1.

Manar Mustafa, "Why we must modify pH value in sol-gel method?" May 24, 2016, 3 pages.

Why and when is it necessary to use carrier DNA/RNA in the extraction procedure? https://www.qiagen.com/gb/resources/faq?id=1b827863-0ce4-4ee4-92e0-219b92c2eb60&lang=en.

Quy Dao Van et al: "Synthesis of Silica-Coated Magnetic Nanoparticles and Application in the Detection of Pathogenic Viruses", Journal of Nanomaterials, vol. 2013, No. 6, Jan. 1, 2013 (Jan. 1, 2013), pp. 1-6, XP055800403, US ISSN: 1687-4110, DOI: 10.1155/2013/603940 Retrieved from the Internet: URL:https://downloads.hindawi.com/journals/jnm/2013/603940.pdf.

International Search Report and Written opinion issued for Application No. PCT/EP2021/058780, dated Aug. 30, 2021.

International Preliminary report on Patentability issued for Application No. PCT/EP2021/058780, dated Oct. 13, 2022.

* cited by examiner

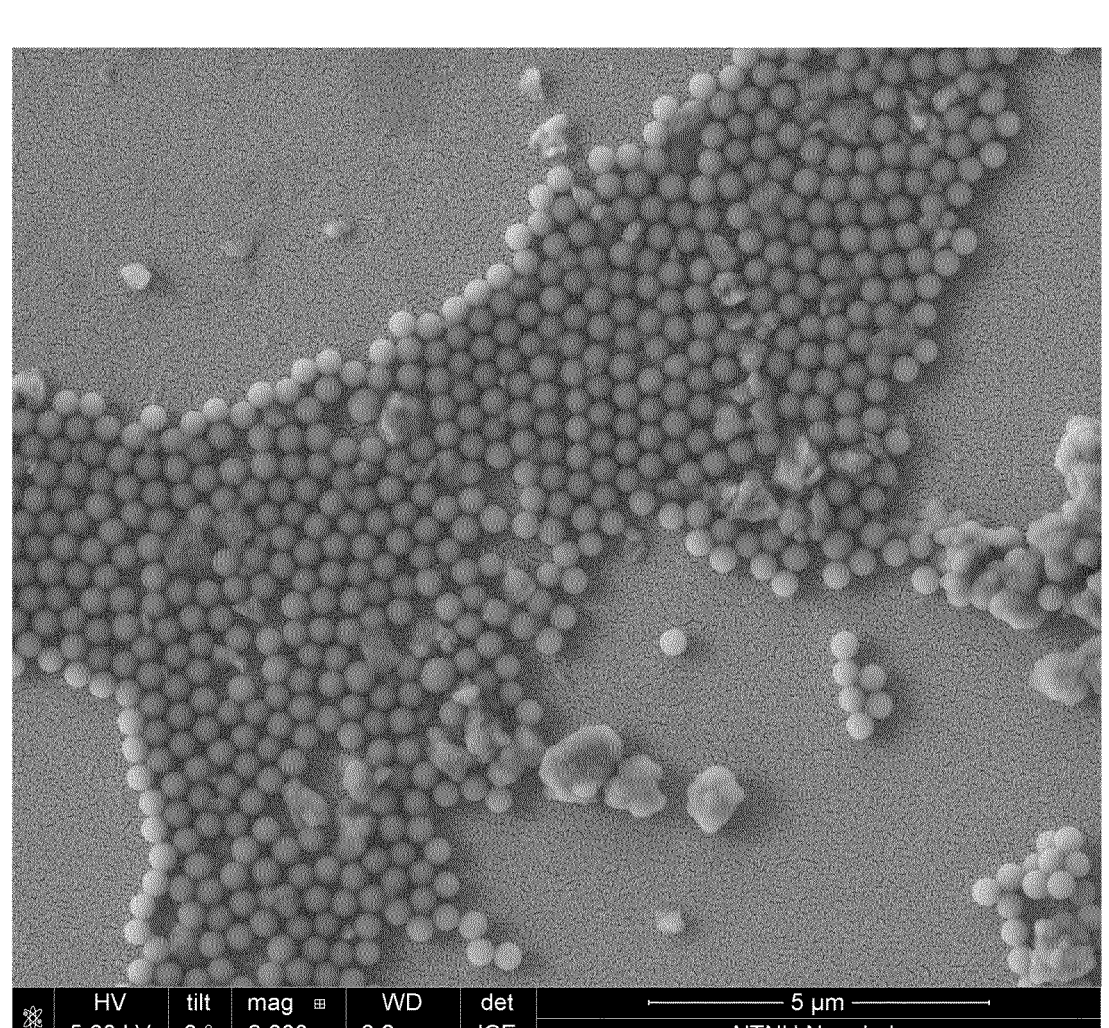

PROCESS FOR PREPARATION OF SILICA COATED MAGNETIC PARTICLES

The present invention relates to methods and products for isolating nucleic acids from samples containing biological material. In particular, the present invention relates to components for use in a method of isolating nucleic acids from a biological sample, particularly lysis and elution buffers that facilitate the capture of nucleic acids on silica-coated magnetic particles and their subsequent release. The invention also provides silica-coated magnetic particles that find particular utility in the methods of isolating nucleic acids and processes for their production, e.g. at a large scale. A kit comprising components for use in a method of isolating nucleic acids from a biological sample, e.g. lysis buffer and silica-coated magnetic particles, is also provided.

Nucleic acid purification and manipulation are essential processes of all molecular biology laboratories. Nucleic acids can be isolated from a wide variety of sources, including samples containing viruses, bacteria, plant or animal cells or tissues. Nucleic acids may also be derived from cell-free sources, such as blood plasma, various environmental sources, or from in vitro reactions. Accordingly, nucleic acids are commonly used as markers for the detection of biological entities, e.g. viruses, bacteria, and may therefore be used in the diagnosis of various diseases. However, nucleic acids typically must be isolated from their environment and amplified before they can be efficiently detected or further manipulated.

Nucleic acid purification techniques commonly utilise commercially produced silica-based columns or require the use of toxic chemicals such as phenol. These techniques generally are not suitable for high-throughput approaches, e.g. because the cost of silica columns makes processing large numbers of samples prohibitively expensive.

Silica-coated magnetic particles are small nano- or microparticles that find utility in nucleic acid purification and manipulation techniques due to their ability to achieve solid-phase reversible immobilisation (SPRI) of nucleic acids. These particles can reversibly bind nucleic acids under dehydrating conditions and readily can be safely immobilised using a strong magnet to facilitate multiple wash and manipulation steps. However, silica-coated magnetic particles typically are produced efficiently in small-scale reactions, e.g. less than 50 ml, meaning their utility on a commercial scale is limited.

The Covid-19 (coronavirus) pandemic has caused health and economic problems on a global scale. One of the main difficulties in controlling the viral outbreak has been detecting the virus, with the demand for detection kits far outstripping the supply. Moreover, the sensitivity of existing detection kits is limited, meaning that subjects tested at an early stage of infection may not produce a positive test result. The failure to positively identify and isolate infected subjects at an early stage has resulted in the unprecedented spread of the Covid-19 virus.

Thus, there is a need for viral detection methods and kits with increased sensitivity and that can be provided on a large scale.

In the work leading to the present invention, it has surprisingly been found that modifications to existing components of nucleic acid extraction kits can significantly enhance the efficiency of nucleic acid isolation using silica-coated magnetic particles and subsequently improve the sensitivity of nucleic acid detection assays. Moreover, it has been found that silica-coated magnetic particles can be efficiently produced on a large scale, whilst retaining advantageous monodispersity and stability properties. The monodispersity properties facilitate the utility of the particles in the efficient capture and isolation of nucleic acids. The long-term stability of the particles makes them particularly useful for the production of nucleic acid detection kits on a commercial scale.

SUMMARY OF INVENTION

Viewed from one aspect the invention provides a process for the preparation of silica coated magnetic particles comprising (I) combining magnetic particles and an alkoxysilane, such as tetraorthoethylsilicate, in water and a $C_{1-4}$-alcohol at a temperature in the range of 70 to 90° C. in the presence of a hydroxide in order to form silica coated magnetic particles;

(II) washing the silica coated magnetic particles of step (I) with water and/or alcohol until the pH of the silica coated magnetic particles, when suspended in water, is between 8 and 11, preferably 9 to 10.

Viewed from another aspect the invention provides a process for the preparation of silica coated magnetic particles comprising (I) combining magnetic particles and an alkoxysilane, such as tetraorthoethylsilicate, in water and a $C_{1-4}$-alcohol at a temperature in the range of 15 to 90° C. in the presence of a hydroxide in order to form silica coated magnetic particles;

(II) washing the silica coated magnetic particles of step (I) with water and/or alcohol until the pH of the silica coated magnetic particles, when suspended in water, is between 8 and 11, preferably 9 to 10.

Viewed from another aspect the invention provides a process for the preparation of a silica coated magnetic particles comprising (I) combining magnetic particles and an alkoxysilane in a $C_{1-4}$-alcohol to form a mixture;

(II) adding water and a hydroxide to the mixture of step (I) and heating the resulting mixture to a temperature in the range of 15 to 90° C., such as 70 to 90° C. in order to form silica coated magnetic particles;

(III) washing the silica coated magnetic particles of step (II) with water and/or alcohol until the pH of the silica coated magnetic particles, when suspended in water, is between 8 and 11.

Viewed from one aspect the invention provides a process for the preparation of silica coated magnetic particles comprising (I) combining magnetic particles and an alkoxysilane, such as tetraorthoethylsilicate, in water and a $C_{1-4}$-alcohol such that the weight ratio of $C_{1-4}$-alcohol to water in the mixture is 1:1 to 15:1 such as 5:1 to 10:1 at a temperature in the range of 15 to 90° C., such as 70 to 90° C. in the presence of a hydroxide in order to form silica coated magnetic particles;

(II) washing the silica coated magnetic particles of step (I) with water and/or alcohol preferably until the pH of the silica coated magnetic particles, when suspended in water, is between 8 and 11, preferably 9 to 10.

Viewed from another aspect the invention provides a process for the preparation of a silica coated magnetic particles comprising (I) combining magnetic particles and an alkoxysilane in a $C_{1-4}$-alcohol to form a mixture;

(II) adding water and a hydroxide to the mixture of step (I) such that the weight ratio of $C_{1-4}$-alcohol to water in the mixture is 1:1 to 15:1, such as 2:1 to 15:1 and heating the resulting mixture to a temperature in the range of 15 to 90° C., such as 70 to 90° C. in order to form silica coated magnetic particles;

(III) washing the silica coated magnetic particles of step (I) with water and/or alcohol solvent, preferably until the pH of the silica coated magnetic particles when suspended in water is between 9 and 10.

Viewed from another aspect the invention provides an aqueous suspension of silica coated magnetic particles wherein said suspension has a pH of 8 to 11, preferably 9 to 10 and the concentration of silica coated magnetic particles in water is 5 to 12 mg/ml.

Viewed from another aspect the invention provides an aqueous suspension of silica coated magnetic particles wherein said suspension has a pH of 8 to 11, preferably 9 to 10 and the concentration of silica coated magnetic particles in water is 5 to 30 mg/ml.

Viewed from another aspect the invention provides an aqueous suspension of silica coated magnetic particles wherein said suspension has a pH of 8 to 11, preferably 9 to 10, and has a zeta potential of –20 to –90 mV, preferably –40 to –70 mV.

Viewed from another aspect the invention provides an aqueous suspension of silica coated magnetic particles wherein the concentration of silica coated magnetic particles in water is 5 to 30 mg/ml, such as 5 to 12 mg/ml and the suspension has a zeta potential of –20 to –90 mV.

Viewed from another aspect the invention provides an aqueous suspension of silica coated magnetic particles wherein said suspension has a pH of 8 to 11, preferably 9 to 10 concentration of silica coated magnetic particles in water is 5 to 30 mg/ml, such as 5 to 12 mg/ml and the suspension has a zeta potential of –20 to –90 mV.

In a further aspect, the inventive provides a lysis solution comprising:

(a) a buffer (e.g. Tris-HCl);

(b) a chelating agent (e.g. EDTA);

(c) a chaotropic agent (e.g. a guanidinium salt, such as guanidinium isothiocyanate); and (d) a detergent (e.g. 2-[4-(2,4,4-trimethylpentan-2-yl)phenoxy] ethanol (Triton X-100) or sodium lauroyl sarcosinate (sarkosyl)); and optionally (e) a reducing agent (e.g. tris(2-carboxyethyl)phosphine (TCEP)); and/or (f) a nucleic acid carrier (e.g. a polymer, such as glycogen).

In another aspect the invention provides the use of a lysis solution as defined herein to release nucleic acids from biological material for adsorption onto the surface of silica-coated magnetic particles, e.g. silica-coated magnetic particles as defined herein.

Viewed from another aspect, the invention provides use of a lysis solution as defined herein in a method of isolating nucleic acids from a sample containing biological material using silica-coated magnetic particles, e.g. silica-coated magnetic particles as defined herein.

In a further aspect, the invention provides a method for isolating nucleic acids from a sample containing biological material comprising:

(a) contacting the sample containing biological material with a lysis solution as defined herein;

(b) contacting the sample from (a) with silica-coated magnetic particles (e.g. as defined herein) under conditions suitable to adsorb nucleic acids in the sample to the silica-coated magnetic particles;

(c) washing the silica-coated magnetic particles from (b); and (d) desorbing (eluting) the nucleic acids from the silica-coated magnetic particles.

Viewed from another aspect, the invention provides an in vitro method of detecting a nucleic acid from an infectious agent in a biological sample comprising:

(a) isolating nucleic acids from a biological sample suspected of containing an infectious agent using the method described herein;

(b) analysing the nucleic acids from (a) for the presence of a nucleic acid from the infectious agent.

In a further aspect, the invention provides an in vitro method of determining whether a subject is infected with an infectious agent comprising:

(a) isolating nucleic acids from a biological sample from a subject suspected of having an infection using the method described herein;

(b) analysing the nucleic acids from (a) for the presence of a nucleic acid from the infectious agent (e.g. virus), wherein detection of a nucleic acid from the infectious agent indicates that the subject has an infection.

In yet another aspect, the invention provides a kit, e.g. for use in a method of isolating nucleic acids from a sample comprising biological material, comprising:

(a) a lysis solution as defined herein; and (b) silica-coated magnetic particles, e.g. as defined herein.

DETAILED DESCRIPTION OF INVENTION

The terms magnetic particles and magnetic beads are used interchangeably herein. In a first aspect, the invention relates to a new process for the preparation of silica coated magnetic particles which are useful on a large scale. The invention also relates to a suspension of silica coated magnetic particles which can be prepared by such a process.

The assay described herein requires the use of magnetic particles that are coated with silica. In order to improve the utility and consistency of the assay it is important that the silica coated magnetic particles are monodisperse, are stable and that they are present in a controlled concentration within the medium in which they are dispersed, typically water. This must be achieved in the context of larger amounts of magnetic particles than would conventionally be used on lab scale. The process of the present invention can be used for scaling up from lab scale to commercial scale, e.g. where the amount of magnetic particles used in the process is at least 300 mg or more, such as 1000 mg or more, such as 300 mg to 1500 mg.

A key aspect of the invention is the development of a process to prepare silica coated magnetic particles that are both monodisperse, highly stable and present in the dispersion in a controlled concentration.

The starting magnetic particles of use in the invention are known. These can be prepared using conventional techniques or purchased from suppliers.

Ideally, magnetic particles of the invention have an average diameter of 50 to 1000 nm before the silica coating is applied, such as 100 to 500 nm. The starting magnetic particles are also preferably monodisperse, e.g. with a CV of 10% or less, especially 5 or less. Preferably the particles are magnetic nanoparticles, i.e. having a diameter of 1000 nm or less, such as 1 to 1000 nm.

Magnetic particles are a class of particle that can be manipulated using magnetic fields. Such particles commonly consist of two components, a magnetic material, often iron, nickel and cobalt, and a chemical component that has functionality. While nanoparticles are preferred, larger particles, called microbeads herein, may have diameters in the range of 0.5-500 micrometers.

The magnetic particles of the present invention preferably comprise an iron oxide, e.g. a mixture of Fe(II) and Fe (III) oxides. Such particles can be made using known processes, e.g. via centrifuging a reaction mixture of iron oxide precursors and base. Suitable iron oxide precursors are other iron salts such as chlorides. Suitable bases are hydroxides such as ammonium hydroxide. A protocol for the preparation of suitable magnetic particles is provided in the examples section and can be readily adapted by the skilled artisan. In a preferred embodiment therefore, the process of the invention uses iron oxide magnetic particles, especially iron oxide nanoparticles (IONP).

The key to providing the desired properties is control of the silica coating process. The process of the invention requires a reaction between the magnetic particles and a silica coating precursor in a temperature controlled reactor to form the coating. By controlling the temperature, we envisage that monodispersity of the coated particles is ensured and the dispersability of the IONPs in the solvent is optimised.

Initially, the silica coating precursor and magnetic particles are combined. This initial combination step may be effected in a $C_{1-4}$-alcohol alone, i.e. without water. It is preferred if the $C_{1-4}$-alcohol is ethanol or isopropanol in all embodiments. At this stage, the temperature of the reaction mixture may be ambient. The actual coating process is only initiated when the water and base is added to hydrolyse the silane. The concentration of magnetic particles in the $C_{1-4}$-alcohol at this point may be 1 to 10 mg/ml. The total amount of magnetic particles present in the reaction mixture may be 100 mg or more such as 200 to 1500 mg.

The silica coating precursor can be any suitable alkoxysilane, such as a tetraalkoxysilane. The alkoxysilane may be of formula $R^1R^2R^3R^4Si$ where $R^1$-$R^2$ are $C_{1-6}$-alkoxy and $R^3$ and $R^4$ are $C_{1-6}$-alkyl or $C_{1-6}$-alkoxy. Ideally all of $R^1$-$R^4$ are alkoxy.

Alkoxy groups of interest are $C_{1-4}$-alkoxy groups such as methoxy or ethoxy. The use of tetraorthoethylsilicate, TEOS, is most preferred.

It is preferred if the silica coating is present in excess in the final silica coated particles. For example, the weight ratio of magnetic particles to silica coating might be 1:1 to 1:10, such as 1:3 to 1:7. The weight of coating can be readily determined by calculating the difference in weight between the starting magnetic particles and those produced in the process. In a most preferred embodiment the weight ratio of magnetic particles to silica coating might be about 1:5. 500 mg of starting magnetic particles might therefore lead to 2.5 g of silica coated magnetic particles. The amount of silica coating precursor added is therefore determined by an analysis of the weight of the magnetic particles in the reaction material and a target ratio of magnetic particles to silica coating.

Water and a hydroxide base is then added to the mixture of magnetic particles and silica coating precursor. The use of ammonium hydroxide is preferred (e.g. in the form of aqueous ammonia). The concentration of the base is not critical. It has however been found that allowing the initial mixture of silica coating precursor and magnetic particles to stir for a period of time, e.g. at least 30 minutes, such as 30 mins to 1.5 hrs before adding the water and hydroxide base improves the monodispersity of the final silica coated particles. In one embodiment therefore, the addition of the water and hydroxide is delayed for at least 30 mins.

It has also been found that increasing the molarity of the hydroxide base leads to larger particles but reduced monodispersity. This offers a way for the skilled person to tailor the particle size and particle size distribution.

The water and hydroxide base can be added together or some of the water might be added and subsequently the base added or vice versa. At this point the temperature may also be increased as herein defined.

The $C_{1-4}$-alcohol to water ratio, in particular the ethanol or isopropanol to water ratio, is important for controlling particle size distribution, i.e. monodispersity. We generally require an excess of $C_{1-4}$-alcohol relative to the water present. We also observe that higher ratios of $C_{1-4}$-alcohol to water are generally required as the amounts of magnetic particles increase in the reaction mixture. In larger scale synthesis however the ratio of $C_{1-4}$-alcohol to water can be lower.

Suitable $C_{1-4}$-alcohol to water ratios may be 1:1 to 15:1, such as 3:2 to 15:1, preferably 2:1 to 15:1, more preferably 3:1 to 12:1, especially 5:1 to 10:1.

Some syntheses, such as large scale syntheses, may operate at a ratio of 3:2 to 6:1, such as 3:2 to 5:1 $C_{1-4}$-alcohol to water.

In one embodiment, these ratios are determined on the amount of additional pure water added. In another embodiment, these ratios are determined on the basis of all the water present, including for example, water present in the base.

Preferred $C_{1-4}$-alcohols are ethanol and isopropanol. The use of isopropanol for larger scale syntheses is especially preferred, e.g. where there is at least 2 L of reaction mixture. A large scale synthesis is therefore regarded as one in which the reaction volume is at least 1.5 L such as 2.0 L or more, e.g. 1.5 to 5.0 L.

It will be appreciated that any water used in the process of the present invention is preferably distilled or at least purified using ion exchanger. It will be appreciated that additional alcohol may be added to ensure that the correct ratio is present although ideally this is not required.

If the $C_{1-4}$-alcohol content is too high then, due to increased concentration of silica coating precursor in the water, the production of free silica particles occurs. Although these free silica particles are readily separated from the magnetic particles during magnetic separation, it is preferred if their formation is avoided.

For monodispersity, temperature is important. We have observed that the reaction of the magnetic particles and the silica coating precursor takes place at a temperature in the range of 70 to 90° C., preferably 75 to 85° C., such as 77 to 83° C., especially 78 to 82° C. A water jacketed heated reactor can suitably be used.

However, higher temperatures are not so important as the reaction synthesis increases in scale. We have observed that the reaction of the magnetic particles and the silica coating precursor can also take place at a temperature in the range of 15 to 90° C., preferably 20 to 85° C., such as 20 to 40° C., especially 20 to 30° C., e.g. when operating on a larger scale synthesis, e.g. where the reaction mixture is at least 2 L in volume.

Without wishing to be limited by theory, it appears that lower temperatures may encourage monodispersity in the final iron particles.

In one embodiment therefore the reaction can be effected at room temperature. It is generally preferred if the temperature at which the reaction is effected is kept constant.

After the reaction is complete (e.g. after 8 hrs or more, preferably 12 hrs or more, such as 12 to 20 hrs), the reaction can be cooled and the magnetic particles can be separated from the reaction medium (conveniently using magnetic separation) and washed. Washing of the particles is effected using water and/or alcohol washes, preferably both water and alcohol washes. Suitable alcohols are $C_{1-4}$-alcohols especially ethanol and isopropanol. The number of these washes may vary. Suitably there are at least two water washes and at least two alcohol washes. Alcohol washes are preferably effected first. A good washing protocol can lead to improvements in particle monodispersity.

A key however to the washing phase is that after washing and suspension in water, the pH should be 8 to 11, especially 9 to 10, more preferably 8.7 to 10.0, more especially 9.0 to 10.0. When the pH is in this range we have surprisingly found that homogeneity and monodispersity of the particles is high. After washing therefore, the silica coated particles are suspended in water for further use.

Moreover, the process of the invention results in an aqueous suspension of silica coated magnetic particles were the zeta potential is of −20 to −90 mV, especially −30 to 70-mV, more preferably −50 to −65 mV, more preferably −55 to −65 mV. The silica coating contains OH groups that can be charged. The zeta potential is a key indicator of the stability of the dispersion. The magnitude of the zeta potential indicates the degree of electrostatic repulsion between adjacent, similarly charged particles and a high zeta potential implies colloidal stability, i.e., the dispersion will resist aggregation. The suspension of the invention is therefore exceptionally stable. The particles may be stable for a period of one month or more, such as 2 to 12 months.

In one embodiment, the process of the invention is a batch, semi-continuous or continuous process, e.g. in which reactants are fed constantly to the reaction vessel and product is constantly removed before step (II) is carried out. In particular, the alkoxysilane and hydroxide base can be fed constantly to the reaction.

The inventors have also found that the relative rates of the base feed (such as ammonium hydroxide feed) and the alkoxysilane feed can generally be varied over a wide range without changing the particle size. It may be, however, that reduced particle sizes can be achieved by increasing the hydroxide flow relative to the alkoxysilane flow.

The silica coated particles produced in the process of the invention preferably have a diameter of 200 to 1000 nm, especially 300 to 700 nm.

The silica coated particles produced in the process of the invention should be monodisperse. Previously, iron oxide particles tended to agglomerate. Monodisperse polymer particles of the invention may have a polydispersity index (PDI) (measured as the square of the standard deviation (SD) divided by the mean, where both SD and mean are respective the particle diameters when these are spheres) may range from 0 to 0.1, such as 0 to 0.01. The PDI is ideally less than 0.005.

Alternatively viewed, monodisperse polymer particles are particles with a coefficient of variation of less than 10%, preferably less than 6% and more preferably less than 5%. Coefficient of variation (CV) is determined in percentage as $$CV=100 \times standard\ deviation/mean$$

where mean is the mean particle diameter and standard deviation is the standard deviation in particle size. CV is preferably calculated on the main mode, i.e. by fitting a monomodal distribution curve to the detected particle size distribution. Thus some particles below or above mode size may be discounted in the calculation which may for example be based on about 90%, more usually about 99% of total particle number (of detectable particles that is). Such a determination of CV is performable on a Field-Effect gun SEM (FE-SEM/FEG-SEM). Polydispersity index can also be determined using such a device.

The present inventors have found that average particle size and particle size distribution can be affected by the presence of an organic polyacid coating or organic polyacid salt coating on the magnetic particles before reaction with the alkoxysilane.

If the magnetic particles are coated with such an organic polyacid or organic polyacid salt coating, such as a citrate coating, the silica coated magnetic particles that form tend to be larger and more monodisperse. The use of the organic polyacid coating or organic polyacid salt on the magnetic particles also appears to reduce the formation of pure silica particles in the synthesis of silica coated magnetic particles.

Without wishing to be limited by theory, it is envisaged that the citrate type coating reduces aggregation and the formation of large clusters. It is therefore preferred if the magnetic particles are coated with an organic polyacid or salt thereof, such as a low molecular weight organic polyacid or salt thereof, e.g. having an Mw of less than 350 g/mol.

Suitable polyacids include citric acid, polylactic acid, glutaric acid, malic acid, maleic acid, succinic acid, fumaric acid, and adipic acid or salts thereof, such as sodium citrate. The use of citric acid or a salt thereof is preferred. The coating is most especially formed from the salt form of these acids, e.g. citrate.

The silica coated particles produced where the magnetic particles have a polyacid or organic polyacid salt type coating may have a diameter of 600 to 2000 nm, especially 800 to 1500 nm.

Coating of the magnetic particles with a polyacid or salt thereof can be accomplished using well known techniques before reaction with the alkoxysilane.

The surface of the magnetic particles can therefore be functionalized by adsorption of the polyacid or salt thereof, such as citric acid/citrate, on the surface of magnetic particles. Citric acid/citrate adsorbs on the surface of the particle by coordinating via one or two of the carboxylate functionalities.

Moreover, the applicant has observed that when higher mass of magnetic particles is used in the preparation process, there is an increased tendency of particle agglomeration. It is therefore desirable to use isopropanol as the C1-4 alcohol to maximise formation of spherical particles. Higher concentration of particles in the reaction mixture may also lead to large final silica coated magnetic particles. Any reaction mixture therefore ideally contains at least 75 mg of magnetic particles.

When the silica coated magnetic particles are used in an assay it is also important that the concentration of particles in a given unit volume is consistent. The present process also gives rise to even concentrations of silica coated magnetic particles in the suspension. Concentrations may lie between 5 to 35 mg/ml, preferably 5 to 30 mg/ml, such as 5 to 25 mg/ml, preferably 5 to 20 mg/ml, such as 5 to 12 mg/ml.

The silica coated magnetic particles formed by the process of the invention can take different geometries. Whilst particles might be essentially spherical, it is also possible for them to be cuboidal or octagonal. Different shaped particles might offer different magnetic properties.

Particle size and shape can be controlled by thermal decomposition of metallic precursors. For example, the precursors can be heated in inert atmosphere (argon or nitrogen) at defined heating rates to temperatures in the range of 150 to 320° C. preceded by degassing the solution.

In general therefore, the particle size and particle size distribution of the final silica coated magnetic particles can be tuned. Options available for fine tuning include changing the nature of alcohol solvent, surface coating of magnetic particles with a polyacid or salt thereof, changing the concentration of hydroxide, and increasing the flow of hydroxide. For example, in certain conditions iso-propanol gives larger size and broader particle size distribution in comparison to ethanol. The citrate coating increases the size of the particles and narrows the particle size distribution. Increases in the concentration of hydroxide decrease the size of the final particles and gives narrow particle size distribution. A key aspect of the invention is therefore the ability to tailor the production process to achieve target silica coated magnetic particles with a particular size and particle size distribution.

In a further aspect, the inventive provides a lysis solution comprising:

(a) a buffer (e.g. Tris-HCl);

(b) a chelating agent (e.g. EDTA);

(c) a chaotropic agent (e.g. a guanidinium salt, such as guanidinium isothiocyanate); and (d) a detergent (e.g. 2-[4-(2,4,4-trimethylpentan-2-yl)phenoxy] ethanol (Triton X-100) or sodium lauroyl sarcosinate (sarkosyl)); and optionally (e) a reducing agent (e.g. tris(2-carboxyethyl)phosphine (TCEP)); and/or (f) a nucleic acid carrier (e.g. a polymer, such as glycogen).

A "lysis solution" refers to a solution (i.e. an aqueous solution comprising the above-mentioned components dissolved in water, e.g. nuclease-free water) that functions to release (e.g. extract) nucleic acids from biological material in a form (e.g. concentration) that can adsorb onto the surface of silica-coated magnetic particles, e.g. silica-coated magnetic particles as defined herein. Thus, a lysis solution as defined herein is for use in releasing nucleic acids from biological material, e.g. in a form that can adsorb onto the surface of silica-coated magnetic particles. In some embodiments, the lysis solution is for use in a method of isolating nucleic acids from a sample containing biological material for capture on silica-coated magnetic particles.

Thus, in some embodiments, the invention provides the use of a lysis solution as defined herein to release nucleic acids from biological material for adsorption onto the surface of silica-coated magnetic particles, e.g. silica-coated magnetic particles as defined herein. Alternatively viewed, the invention provides use of a lysis solution as defined herein in a method of isolating nucleic acids from a sample containing biological material using silica-coated magnetic particles, e.g. silica-coated magnetic particles as defined herein.

A "sample containing biological material" (e.g. a biological sample) refers to a sample containing material directly or indirectly obtained from an organism or virus. Biological material may thus comprise all types of mammalian and non-mammalian animal cells, plant cells, algae including blue-green algae, fungi, bacteria, protozoa, viruses etc. In particular, it refers to material comprising one or more nucleic acids. In some preferred embodiments, the material contains one or more viral, bacterial, fungal or parasite nucleic acids. Thus, in some embodiments, a sample containing biological material comprises one or more cells from an organism. However, the biological material need not contain cells, e.g. it may be a cell-free sample such as blood plasma. It will be evident that a biological material from any organism could be used in the invention, e.g. plant, animal or fungal. In some preferred embodiments, the biological material is from an animal, particularly from a human.

Biological and clinical samples include any cell or tissue sample of an organism (eukaryotic, prokaryotic), or any body fluid or preparation derived therefrom, as well as samples such as cell cultures, cell preparations, cell lysates etc. Biological material may be derived or obtained, e.g. purified, from environmental samples, e.g. soil and water samples or food samples. The biological material (e.g. biological or clinical samples) may be freshly prepared or obtained, or it may be prior-treated in any convenient way, e.g. for storage. In some embodiments, the biological material is processed (e.g. diluted) to provide a solution that can be contacted with the lysis solution of the invention. The biological material may be processed to provide a buffered solution (e.g. a buffered solution comprising the same buffer as the lysis solution) comprising the biological material, i.e. for use in the methods described herein.

The biological material may thus be a harvested or biopsied sample or a cultured sample. Representative samples include clinical samples, e.g. oral samples (e.g. saliva, material from a cheek swab, expectorate, mucus, phlegm, sputum etc.), nasal samples (e.g. mucus, material from a nasal swab etc.), whole blood or blood-derived products, blood cells, tissues, biopsies, spinal fluid, tears, urine, faeces or cultured tissues or cells etc. including cell suspensions.

The inventors have determined that the lysis solution described herein finds particularly utility in releasing nucleic acids, particularly viral nucleic acids, from oral and nasal samples. Thus, in some preferred embodiments, the biological material is or contains an oral and/or nasal sample as defined above, e.g. mucus, sputum or phlegm.

The buffer functions to maintain the lysis solution at a constant pH. Any buffer suitable for use with nucleic acids, e.g. used in nucleic acid extraction and isolation methods, may be used in the lysis solution of the invention. In some embodiments, the buffer is Tris (tris(hydroxymethyl) aminomethane), e.g. Tris-HCl, or a citrate buffer, e.g. Sodium or Potassium citrate.

The pH of the lysis solution may be between about 6.0-9.0, preferably between about 6.5-8.5, such as about 7.4-8.2, e.g. about 7.5, 7.6, 7.7, 7.8, 7.9, 8.0 or 8.1. In some preferred embodiments, the pH of the lysis solution is about 7.8.

The concentration of the buffer in the lysis solution will be dependent on the buffer used and must be sufficient to maintain the lysis solution at a constant pH as defined above. The skilled person readily could select a suitable concentration range. In some embodiments, the buffer concentration in the lysis solution is about 10-200 mM, e.g. about 25-100 mM, 30-90 mM, 35-80 mM, 40-70 mM, e.g. about 45-60 mM, such as about 50 mM. Thus, in some embodiments, the lysis solution comprises about 40-60 mM (e.g. about 50 mM) Tris (e.g. Tris-HCl), at a pH defined above, e.g. about 6.5-8.5, e.g. about 7.8.

The chelating agent functions to sequester divalent cations, which are essential for enzymes that act on nucleic acids, e.g. DNases and RNases. Thus, the chelating agent functions to inhibit or prevent the degradation of nucleic acids in the sample. Accordingly, the chelating agent comprises a chelator of divalent cations, for example EDTA (Ethylenediaminetetraacetic acid).

The chelating agent is present in the lysis solution at a concentration sufficient to inhibit nucleic acid degrading enzymes (i.e. in the sample comprising biological material), e.g. about 5-50 mM, such as about 10-40 mM or about 15-30 mM, e.g. about 20 mM. Thus, in some embodiments, the lysis solution comprises EDTA at a concentration as defined above.

Chaotropic agents denature macromolecules in the biological material, such as proteins and nucleic acids. Chaotropic agents also disrupt membrane lipids. Thus, the chaotropic agents in the lysis solution function to reduce enzymatic activity and facilitate the induction of cell lysis. Any suitable chaotropic agent may be used in the lysis solution. For instance, in some embodiments, the chaotropic agent is selected from a guanidinium salt (e.g. guanidinium isothiocyanate or guanidinium chloride), lithium perchlorate, lithium acetate, magnesium chloride, n-butanol, ethanol, phenol, 2-propanol, sodium dodecyl sulfate, thiourea, urea and a combination thereof.

In a preferred embodiment, the chaotropic agent is a guanidinium salt, preferably guanidinium isothiocyanate.

The chaotropic agent is present in the lysis solution at a concentration sufficient to denature macromolecules in the biological material and/or induce cell lysis. In some embodiments, the lysis solution contains a guanidinium salt at a concentration of at least about 3M, such as at least about 3.5M or about 4.0M, e.g. about 3-6M. In a preferred embodiment, the lysis solution contains guanidinium isothiocyanate at a concentration of about 3.5-4.5M, e.g. about 4.0M.

The detergent in the lysis solution functions to disrupt cellular and organelle membranes, e.g. lyse cells and organelles, and to denature proteins in the biological material. Thus, detergents function to facilitate the release of nucleic acids from cells and other entities, e.g. viruses, in the biological material. Any suitable detergent may be used in the lysis solution, e.g. a non-ionic detergent. For instance, in some embodiments, the detergent is selected from sodium lauroyl sarcosinate (sarkosyl), sodium dodecyl sulfate (SDS), 4-(1,1,3,3-Tetramethylbutyl)phenyl-polyethylene glycol, 2-[4-(2,4,4-trimethylpentan-2-yl)phenoxy] ethanol (Triton X-100) and a combination thereof. In a preferred embodiment, the detergent is selected from sodium lauroyl sarcosinate (sarkosyl) and 2-[4-(2,4,4-trimethylpentan-2-yl) phenoxy] ethanol (Triton X-100).

The detergent is present in the lysis solution at a concentration sufficient to disrupt cellular and organelle membranes, e.g. lyse cells and organelles, disrupt viral envelopes and/or capsids, and/or to denature proteins in the biological material. In some embodiments, the detergent is present at a concentration of about 0.5-5.0% w/v, e.g. about 0.75-4.5% w/v, about 1.0-4.0% w/v, about 1.5-3.0% w/v, such as about 1.75-2.25% w/v, e.g. about 2.0%. In some preferred embodiments, the detergent is sodium lauroyl sarcosinate (sarkosyl) or 2-[4-(2,4,4-trimethylpentan-2-yl)phenoxy] ethanol (Triton X-100) at a concentration as defined above.

The reducing agent, when present in the lysis solution, functions to reduce disulfide bonds in proteins in the biological material. Suitable reducing agents are well-known in the art and may be selected from tris(2-carboxyethyl)phosphine (TCEP), dithiothreitol (DTT), β-mercaptoethanol (β-ME) and a combination thereof.

The inventors have found that the use of TCEP is particularly advantageous because it has high stability and activity at room temperature, thereby facilitating the production of a lysis solution with improved activity that can be stored long term (e.g. useful for large scale production of a commercial product). Thus, in some preferred embodiments, the reducing agent is TCEP. As shown in the Examples, lysis solution containing TCEP is particularly effective at isolating RNA from clinical samples, e.g. oral samples.

While it may be advantageous to include a reducing agent in the lysis solution in some embodiments, the inventors have unexpectedly determined that it is not necessary to include a reducing agent in the lysis solution, particularly when the lysis solution is used to release nucleic acids from oral or nasal samples.

The reducing agent, when included in the lysis solution, is present at a concentration sufficient to reduce disulfide bonds in proteins in the biological material. In some embodiments, the reducing agent is present in the lysis solution at a concentration of about 1-20 mM, such as about 2-19 mM, 3-18 mM, 4-17 mM or about 5-16 mM, e.g. about 6, 7, 8, 9, 10, 11, 12, 13, 14 or 15 mM, preferably about 10 mM. However, in some embodiments, a higher amount of reducing agent may be used, e.g. about 20-150 mM, such as about 25-125 mM or about 30-100 mM, e.g. about 80 mM. Thus, in some embodiments, the lysis solution comprises TCEP at a concentration as defined above.

The nucleic acid carrier, when present in the lysis solution, functions to increase the concentration of nucleic acids in the sample. This facilitates alcohol mediated aggregation of nucleic acids and adsorption onto the silica-coated magnetic particles. Nucleic acid carriers typically are polymers, such as nucleic acids or polysaccharides. For instance, a nucleic acid carrier may be selected from glycogen, sonicated DNA (e.g. sonicated calf thymus or salmon sperm DNA), poly dT and/or poly dA, tRNA, polyacrylamide (e.g. linear polyacrylamide) and a combination thereof.

The inventors have found that the use of glycogen is particularly advantageous because it is an inert molecule that does not interfere with downstream nucleic acid reactions, e.g. amplification and/or detection reactions.

Thus, in some preferred embodiments, the nucleic acid carrier is glycogen. Glycogen is a highly branched glucose polymer, which may be obtained from any suitable source, e.g. extracted from oysters, and is commercially available. Thus, the glycogen in the lysis solution comprises a mixture of glucose polymers, wherein each polymer may contain up to 50,000 glucose molecules, having a molecular weight of up to about 8 MDa.

The nucleic acid carrier, when included in the lysis solution, is present in the lysis solution at a concentration sufficient to increase the recovery of nucleic acids from the biological material, i.e. to increase the adsorption of the nucleic acids on to the silica-coated magnetic particles. In some embodiments, the nucleic acid carrier is present in the lysis solution at a concentration of about 0.1-5 mg/ml, such as about 0.2-4.5 mg/ml, 0.3-4.0 mg/ml, 0.4-3.5 mg/ml or about 0.5-3.0 mg/ml, e.g. about 0.6, 0.7, 0.8, 0.9, 1.0, 1.1, 1.2, 1.3, 1.4 or 1.5 mg/ml, preferably about 1.0 mg/ml. Thus, in some embodiments, the lysis solution comprises glycogen at a concentration as defined above.

While it may be advantageous to include a nucleic acid carrier in the lysis solution in some embodiments, the inventors have determined that it is not essential to include a nucleic acid carrier in the lysis solution. In particular, when the lysis solution is used to release nucleic acids from samples that contain a high concentration of the nucleic acid(s) to be detected, a nucleic acid carrier may not be required. For instance, some biological samples (e.g. oral and nasal samples) may contain high concentrations of viral nucleic acids (e.g. coronavirus (e.g. Covid-19) nucleic acids), thereby obviating the need to include a nucleic acid carrier in the lysis solution. However, in some embodiments, the lysis solution contains a nucleic acid carrier, such as glycogen.

As discussed further below, the lysis solution may also comprise a proteinase, e.g. proteinase K. However, in preferred embodiments, the proteinase is not added to the lysis solution until the solution has been contacted with a sample containing biological material.

Thus, in some embodiments, the lysis solution comprises:
(a) a buffer (e.g. Tris) at a concentration of about 10-200 mM, preferably 40-60 mM, with a pH of about 6.0-9.0, preferably about 7.4-8.2;
(b) a chelating agent (e.g. EDTA) at a concentration of about 5-50 mM, preferably about 10-30 mM or about 15-25 mM;
(c) a chaotropic agent (e.g. a guanidinium salt) at a concentration of at least about 3M, preferably about 3-6M; and
(d) a detergent (e.g. sodium lauroyl sarcosinate (sarkosyl) or 2-[4-(2,4,4-trimethylpentan-2-yl)phenoxy] ethanol (Triton X-100)) at a concentration of about 0.5-5.0% w/v, preferably about 0.75-3.0% w/v, such as about 1.0-1.5% w/v (e.g. for Triton X-100) or 1.75-2.25% w/v (e.g. for sarkosyl).

Thus, in some embodiments, the lysis solution comprises:
(a) a buffer (e.g. Tris) at a concentration of about 10-200 mM, preferably 40-60 mM, with a pH of about 6.0-9.0, preferably about 7.4-8.2;
(b) a chelating agent (e.g. EDTA) at a concentration of about 5-50 mM, preferably about 10-30 mM or about 15-25 mM;
(c) a chaotropic agent (e.g. a guanidinium salt) at a concentration of at least about 3M, preferably about 3-6M; and
(d) a detergent (e.g. sodium lauroyl sarcosinate (sarkosyl) or 2-[4-(2,4,4-trimethylpentan-2-yl)phenoxy] ethanol (Triton X-100)) at a concentration of about 0.5-5.0% w/v, preferably about 0.75-3.0% w/v, such as about 1.0-1.5% w/v (e.g. for Triton X-100) or 1.75-2.25% w/v (e.g. for sarkosyl); and
(e) a nucleic acid carrier (e.g. glycogen) at a concentration of about 0.1-5 mg/ml, preferably about 0.5-3.0 mg/ml.

Thus, in some embodiments, the lysis solution comprises:
(a) a buffer (e.g. Tris) at a concentration of about 10-200 mM, preferably 40-60 mM, with a pH of about 6.0-9.0, preferably about 7.4-8.2;
(b) a chelating agent (e.g. EDTA) at a concentration of about 5-50 mM, preferably about 15-30 mM;
(c) a chaotropic agent (e.g. a guanidinium salt) at a concentration of at least about 3M, preferably about 3-6M;
(d) a detergent (e.g. sodium lauroyl sarcosinate (sarkosyl) or 2-[4-(2,4,4-trimethylpentan-2-yl)phenoxy] ethanol (Triton X-100)) at a concentration of about 0.5-5.0% w/v, preferably about 0.75-3.0% w/v, such as about 1.0-1.5% w/v (e.g. for Triton X-100) or 1.75-2.25% (e.g. for sarkosyl) w/v;
(e) a reducing agent (e.g. tris(2-carboxyethyl)phosphine (TCEP)) at a concentration of about 1-20 mM, preferably about 5-16 mM; and
(f) a nucleic acid carrier (e.g. glycogen) at a concentration of about 0.1-5 mg/ml, preferably about 0.5-3.0 mg/ml.

The components of the lysis solution may be independently selected from any of the components listed above. Preferred components are provided as examples in the embodiment above. In some embodiments, the lysis solution comprises glycogen as defined above. In some embodiments, the lysis solution comprises TCEP and glycogen as defined above.

In a preferred embodiment, the lysis solution comprises:
(a) Tris-HCl at a concentration of about 40-60 mM (e.g. about 50 mM), with a pH of about 7.4-8.2 (e.g. about 7.8);
(b) EDTA at a concentration of about 15-30 mM (e.g. about 20 mM);
(c) a guanidinium salt (e.g. guanidinium isothiocyanate) at a concentration of about 3-6M (e.g. about 4M); and
(d) sodium lauroyl sarcosinate at a concentration of about 1.75-2.25% w/v (e.g. about 2.0% w/v) or Triton-X100 at a concentration of about 0.75-1.50% w/v (e.g. about 1.2% w/v).

In a further preferred embodiment, the lysis solution comprises:
(a) Tris-HCl at a concentration of about 40-60 mM (e.g. about 50 mM), with a pH of about 7.4-8.2 (e.g. about 7.8);
(b) EDTA at a concentration of about 15-30 mM (e.g. about 20 mM);
(c) a guanidinium salt (e.g. guanidinium isothiocyanate) at a concentration of about 3-6M (e.g. about 4M); and
(d) sodium lauroyl sarcosinate at a concentration of about 1.75-2.25% w/v (e.g. about 2.0% w/v) or Triton-X100 at a concentration of about 0.75-1.50% w/v (e.g. about 1.2% w/v); and
(e) glycogen at a concentration of about 0.5-3.0 mg/ml (e.g. about 1.0 mg/ml).

In a particularly preferred embodiment, the lysis solution comprises:
(a) Tris-HCl at a concentration of about 40-60 mM (e.g. about 50 mM), with a pH of about 7.4-8.2 (e.g. about 7.8);
(b) EDTA at a concentration of about 15-30 mM (e.g. about 20 mM);
(c) a guanidinium salt (e.g. guanidinium isothiocyanate) at a concentration of about 3-6M (e.g. about 4M);
(d) sodium lauroyl sarcosinate at a concentration of about 1.75-2.25% w/v (e.g. about 2.0% w/v) or Triton-X100 at a concentration of about 0.75-1.50% w/v (e.g. about 1.2% w/v);
(e) TCEP at a concentration of about 5-16 mM (e.g. about 10 mM); and
(f) glycogen at a concentration of about 0.5-3.0 mg/ml (e.g. about 1.0 mg/ml).

In some embodiments, the detergent in the lysis solution as defined above is Triton X-100.

In some embodiments, the lysis solution further comprises a proteinase, e.g. proteinase K, as defined further below.

The invention allows the isolation (e.g. capture and purification) of any nucleic acids, i.e. RNA or DNA, from any sample containing biological material as defined above. The invention is particularly suitable for isolating and analysing nucleic acids from clinical samples, such as oral and nasal samples, e.g. for the detection of nucleic acids associated with a disease, e.g. infection, such as a viral, bacterial, fungal or parasitic infection.

Thus, in a further aspect, the invention provides a method for isolating nucleic acids from a sample containing biological material comprising:
(a) contacting the sample containing biological material with a lysis solution as defined herein;
(b) contacting the sample from (a) with silica-coated magnetic particles (e.g. as defined herein) under conditions suitable to adsorb nucleic acids in the sample to the silica-coated magnetic particles;
(c) washing the silica-coated magnetic particles from (b); and (d) desorbing (eluting) the nucleic acids from the silica-coated magnetic particles.

The step of contacting the sample containing biological material with the lysis solution may be performed using any conditions suitable to result in the release (extraction) of nucleic acids from the biological material, e.g. to result in cell, organelle and/or viral lysis. By way of example, suitable conditions may be contacting the sample with at least an equal volume of lysis solution, preferably an excess of lysis solution (e.g. at least about two volumes of the sample containing the biological material) at any suitable temperature, such as about 10-37° C., e.g. about 15-30 such as about 10, 12, 15, 18, 20, 22, 25, 28, 30, 33, 35 or 37° C., e.g. about room temperature, e.g. about 20-25° C. The step may be performed for at least about 5 minutes.

The step of contacting the sample from (a), i.e. the lysed sample, with silica-coated magnetic particles (e.g. as defined herein), may be performed using any conditions suitable to result in the adsorption of nucleic acids released from the biological material onto the silica-coated magnetic particles. In a representative example, the sample from (a) is contacted with at least an equal volume of a suspension of magnetic particles, preferably an excess of a suspension of magnetic particles (e.g. about 1.1-5, such as 1.15-4, 1.20-3 or 1.25-2 volumes of the sample from (a), e.g. 2-4 or 3-4 volumes of the sample from (a)) under the same temperature conditions as step (a) as defined above. In some embodiments, the suspension of magnetic particles is chilled to enhance nucleic acid aggregation and/or to reduce nucleic acid degradation. Thus, in some embodiments, the suspension of magnetic particles may be at about 10° C. or less, e.g. about 4° C. or less, e.g. −20° C. to 10° C.

The magnetic particles may be suspended in any liquid suitable to result in the aggregation of nucleic acids and adsorption to the silica-coating (e.g. dehydrating conditions). For instance, the magnetic particles may be suspended in a $C_2$-$C_4$ alcohol optionally comprising a salt. In some embodiments, the magnetic particles are suspended in isopropanol or a solution comprising at least 70% ethanol (e.g. 80, 90, 95 or 100% ethanol), optionally further comprising a salt, such as an acetate salt, e.g. sodium or potassium acetate. In a preferred embodiment, the magnetic particles are suspended in isopropanol.

The magnetic particles are contacted with the sample from (a) in excess, i.e. such that all or substantially all (e.g. at least 70%, 80% or 90%) of the nucleic acids in the sample may be adsorbed on the silica-coating. In some embodiments, the concentration of magnetic particles in the suspension is at least about 0.25 mg/ml, e.g. at least about 0.3, 0.4, 0.5, 0.6, 0.7, 0.8 or 0.9 mg/ml. Thus, in some embodiments, the concentration of magnetic particles in the suspension is about 0.25-0.8 mg/ml, 0.30-0.7 mg/ml or 0.4-0.6 mg/ml, e.g. about 0.45-0.55 mg/ml, preferably about 0.5 mg/ml.

The suspended magnetic particles may optionally contain other components, e.g. a proteinase, to enhance the efficiency of the RNA extraction. In some embodiments, the suspension of magnetic particles contains proteinase K at a concentration of about 20-250 µg/ml, e.g. about 50-150 µg/ml or 75-125 µg/ml, such as about 100 µg/ml.

However, in some embodiments, the proteinase may be included in the lysis solution. Alternatively, in some embodiments, the proteinase may be added to the sample after it has been contacted with the lysis solution (i.e. lysis solution not containing the proteinase) but before it is contacted with the suspension of magnetic particles. In some embodiments, the proteinase may be added contemporaneously with the suspension of magnetic particles. Thus, in some embodiments, the method comprises a further step of contacting the sample from (a) with a proteinase, e.g. proteinase K. The proteinase may be added in an amount to achieve a concentration as defined above.

Thus, in some embodiments, the suspension of magnetic particles contacted with the sample from (a) comprises: (i) silica-coated magnetic particles (e.g. as defined herein) suspended in isopropanol at a concentration of at least about 0.25 mg/ml, e.g. about 0.25-0.8 mg/ml, 0.30-0.7 mg/ml or 0.4-0.6 mg/ml; and (ii) proteinase K at a concentration of about 20-250 µg/ml.

In some embodiments, the suspension of magnetic particles is contacted with the sample from (a) after the addition of a proteinase to the sample and comprises silica-coated magnetic particles (e.g. as defined herein) suspended in isopropanol at a concentration of at least about 0.25 mg/ml, e.g. about 0.4-0.6 mg/ml.

In a preferred embodiment, the proteinase K is P06873/ PRTK_PARAQ, which refers to the UniProtKB/Swiss-Prot accession numbers, or a functional variant or derivative thereof or a combination thereof.

The mixture from step (b) may be treated to keep the magnetic particles in suspension, e.g. the mixture is agitated. This may be achieved by any suitable means, e.g. pipetting, shaking or vortexing the mixture. In some embodiments, the mixture is agitated for at least about 10 minutes, preferably at least about 15 minutes.

The step of washing the washing the silica-coated magnetic particles from (b), i.e. on which the nucleic acids are adsorbed, may be achieved using any suitable means. The use of magnetic particles facilitates the washing and subsequent steps as the particles can be aggregated using a magnet to enable the removal of the liquid phase (supernatant). Thus, the step of washing comprises a step of removing the supernatant from the mixture, contacting the magnetic particles with a suitable washing liquid and agitating the mixture, e.g. for at least about 1 minute. A suitable washing liquid is preferably a $C_2$-$C_4$ alcohol, such as isopropanol or a solution comprising ethanol, e.g. at least about 70% ethanol, e.g. 80% ethanol. In some embodiments, the volume of washing liquid added to the magnetic particles is equivalent to the volume of the suspension of magnetic particles used in step (b).

The wash step(s) may be repeated multiple times, e.g. 2, 3, 4, 5 or more times. Alternatively viewed, in some embodiments the method comprises multiple wash steps, wherein the same or different washing conditions may be used in each step.

In some embodiments, the wash step comprises washing the magnetic particles with isopropanol followed by at least one wash with 80% ethanol, preferably two washes with 80% ethanol.

The temperature of the washing steps may be determined readily by a person of skill in the art based on routine experimentation. In some embodiments, the washing steps are performed at 10° C. or less, e.g. 9, 8, 7, 6, 5 or 4° C. or less.

After the final wash step, the magnetic particles may be dried prior to eluting the nucleic acids. Thus, in some embodiments, the method comprises a step of drying the magnetic particles, e.g. at room temperature for about 10 minutes.

The step of desorbing (eluting) the nucleic acids from the silica-coated magnetic particles may be achieved by any suitable means. In a representative embodiment, the step of desorbing (eluting) comprises rehydrating the magnetic particles, e.g. contacting the magnetic particles with an aqueous elution solution and agitating the mixture, e.g. for at least about 5 minutes. A suitable elution solution is water (nuclease-free water) optionally comprising a buffer suitable for nucleic acids, as described above.

The volume of elution solution used in step (d) may readily be determined by the skilled person. In a representative embodiment, the volume of elution solution used in step (d) is equivalent to the volume of the sample or less, e.g. about 80, 70 or 60% of the volume of the sample or less, e.g. about 50% of the volume of the sample.

The inventors have surprisingly found that the amount of nucleic acid obtained (e.g. recovered) from the silica-coated magnetic particles may be increased using an elution solution containing a blocking reagent, such as a non-ionic surfactant, particularly a non-ionic detergent.

In some embodiments, the non-ionic detergent is a polysorbate, such as Polyoxyethylene sorbitan monolaurate (Tween). In some embodiments, the non-ionic detergent is Polyoxyethylene (20) sorbitan monolaurate (Tween 20). Other suitable blocking reagents include serum proteins (e.g. bovine serum albumin), nonyl phenoxypolyethoxylethanol (NP-40) or a combination thereof.

The concentration of the blocking reagent in the elution solution is sufficient to enhance the recovery of nucleic acids from the magnetic particles compared to the elution solution without the blocking reagent and may be determined using routine experimentation. In some embodiments, the elution solution comprises a blocking reagent at a concentration of about 0.1-5% v/v, e.g. about 0.5-3% v/v, such as about 0.75-1.25% v/v, e.g. about 1.0% v/v. In a preferred embodiment, the elution solution comprises Polyoxyethylene (20) sorbitan monolaurate (Tween 20) at a concentration as defined above.

Thus, in some embodiments, the invention provides an elution solution for desorbing nucleic acids from silica-coated magnetic particles comprising an aqueous solution comprising a blocking reagent as defined above.

Any suitable blocking reagent may be used in the elution buffer. Whilst not wishing to be bound by theory, it is hypothesised that the blocking reagent may enhance the amount of nucleic acid recovered from the magnetic particles by blocking sites in the vessel (e.g. tube or plate) in which the elution step takes place. This may prevent nucleic acids released from the silica-coating from binding to the vessel, thereby increasing the amount of nucleic acids in solution.

The temperature of the desorption step may be determined readily by a person of skill in the art based on routine experimentation. In some embodiments, the desorption (elution) step is performed at 10° C. or less, e.g. 9, 8, 7, 6, 5 or 4° C. or less.

Following elution from the magnetic particles, the solution comprising the nucleic acids is separated from the magnetic particles, e.g. for further processing, such as amplification and/or analysis. Thus, in some embodiments, the method comprises a step of separating the solution comprising nucleic acids from the magnetic particles.

The term "nucleic acid" refers to molecules made up of ribonucleotides and/or deoxyribonucleotides as well as synthetic nucleotide residues that are capable of participating in Watson-Crick type or analogous base pair interactions, i.e. "hybridisation" or the formation of a "duplex". Thus, the nucleic acid may be DNA or RNA or any modification thereof, e.g. PNA or other derivatives containing nonnucleotide backbones. In preferred embodiments, the nucleic acid is a naturally-occurring molecule, i.e. DNA or RNA.

The invention may be used to isolate DNA (e.g. genomic DNA) and/or RNA. Thus, in some embodiments, the invention relates to the isolation of total nucleic acid (TNA) from biological material.

In embodiments in which DNA is isolated, the DNA may be any DNA molecule which may occur in biological material, e.g. in a cell. In some embodiments, the DNA is viral DNA, bacterial DNA (e.g. plasmid DNA), fungal DNA or parasite DNA. In some embodiments, the DNA is genomic, i.e. nuclear, DNA, mitochondrial DNA or plastid DNA, e.g. chloroplast DNA. In a preferred embodiment, the DNA is viral, bacterial, fungal or parasite DNA, particularly viral or bacterial DNAI.

The RNA may be any RNA molecule which may occur in biological material, e.g. in a cell. Thus it may be viral RNA, mRNA, tRNA, rRNA, small nuclear RNA (snRNA), small nucleolar RNA (snoRNA), microRNA (miRNA), small interfering RNA (siRNA), piwi-interacting RNA (piRNA), ribozymal RNA, antisense RNA or non-coding RNA. The RNA may be from any organism. In some preferred embodiments, the RNA is viral RNA, e.g. from a coronavirus, such as Covid-19 (severe acute respiratory syndrome coronavirus 2 (SARS-CoV2)).

In some embodiments, it may be desirable to isolate only one type of nucleic acid from a sample containing biological material, e.g. DNA or RNA. Thus, in some embodiments, the nucleic acids may be treated to selectively degrade one type of nucleic acid, e.g. by contacting the nucleic acids with an endonuclease, e.g. an RNase or DNase. In some embodiments, the step of degrading one type of nucleic acid may be performed when the nucleic acids are adsorbed on the silica-coated magnetic particles, e.g. by contacting the particles with an endonuclease following the wash steps. Following the step of degrading one type of nucleic acid, the magnetic particles may be subjected to further wash steps (e.g. as defined above) to remove the degradation products and endonuclease, prior to elution.

Isolated nucleic acids obtained from the method may be processed and manipulated using standard molecular biology techniques that are well-established in the art. In some embodiments, the nucleic acids obtained from the method may be concentrated, diluted, pooled (e.g. with nucleic acids obtained from other samples), amplified and/or analysed.

As shown in the Examples below, the method for isolating nucleic acids from a sample containing biological material is particularly effective for isolating viral nucleic acids, e.g. viral RNA, such as RNA from a coronavirus (e.g. Covid-19 (SARS-CoV2)).

Thus, in some embodiments, the invention provides an in vitro method of detecting a nucleic acid from an infectious agent in a biological sample (e.g. an oral and/or nasal sample) comprising:

(a) isolating nucleic acids from a biological sample suspected of containing an infectious agent (e.g. a virus, such as a coronavirus) using the method described herein;

(b) analysing the nucleic acids from (a) for the presence of a nucleic acid from the infectious agent.

Thus, more particularly, the invention provides an in vitro method of detecting a viral nucleic acid (e.g. RNA, e.g. coronavirus RNA) in a biological sample (e.g. an oral and/or nasal sample) comprising:

(a) isolating nucleic acids from a biological sample suspected of containing a viral nucleic acid using the method described herein;

(b) analysing the nucleic acids from (a) for the presence of a viral nucleic acid.

Alternatively viewed, the invention provides an in vitro method of determining whether a subject is infected with an infectious agent (e.g. a virus, such as a coronavirus) comprising:

(a) isolating nucleic acids from a biological sample (e.g. an oral and/or nasal sample) from a subject suspected of having an infection using the method described herein;

(b) analysing the nucleic acids from (a) for the presence of a nucleic acid from the infectious agent (e.g. virus, such as a coronavirus), wherein detection of a nucleic acid from the infectious agent indicates that the subject has an infection.

In some embodiments, the method may further comprise a step of treating the infected subject, e.g. with an antiviral drug, antibiotic, vaccine or other suitable therapeutic agent.

An "infectious agent" may be defined as any disease-causing organism or virus. In some instances, an infection may be characterised by the reaction of the subject (e.g. organ or tissues of said subject) to said organisms or viruses and, in some cases, to the toxins produced by said organisms. An infectious agent may be a microbe, virus or parasite and the infection and may be local or systemic. A microbial infection may be any bacterial or fungal infection, i.e. caused by a bacterium or fungus.

In some embodiments, the infectious agent may be a virus, e.g. a DNA or RNA virus, selected from Australian bat lyssavirus, Banna virus, Barmah forest virus, Bunyamwera virus, Bunyavirus La Crosse, Bunyavirus snowshoe hare, Coronavirus (e.g. Covid-19 (SARS-CoV2)), Cercopithecine herpesvirus, Chikungunya virus, Crimean-Congo hemorrhagic fever virus, Dengue virus, Dhori virus, Dugbe virus, Duvenhage virus, Eastern equine encephalitis virus, Ebolavirus, Echovirus, Encephalomyocarditis virus, European bat lyssavirus, Hantaan virus, Hendra virus, Hepatitis A virus, Hepatitis B virus, Hepatitis C virus, Hepatitis E virus, Hepatitis delta virus, Human herpesvirus 1, Human adenovirus, Human astrovirus, Human coronavirus, Human cytomegalovirus, Human enterovirus 68-70, Human herpesvirus 2, Human herpesvirus 6, Human herpesvirus 7, Human herpesvirus 8, Human immunodeficiency virus, Human parainfluenza, Human parvovirus B19, Human respiratory syncytial virus, Human rhinovirus, Human SARS coronavirus, Human T-lymphotropic virus, Human torovirus, Influenza A virus, Influenza B virus, Influenza C virus, Isfahan virus, JC polyomavirus, Japanese encephalitis virus, Junin arenavirus, KI Polyomavirus, Kunjin virus, Lagos bat virus, Lake Victoria marburgvirus, Langat virus, Lassa virus, Lordsdale virus, Louping ill virus, Lymphocytic choriomeningitis virus, Machupo virus, Mayaro virus, Measles virus, Mengo encephalomyocarditis virus, Mokola virus, Molluscum contagiosum virus, Monkeypox virus, Mumps virus, Murray valley encephalitis virus, New York virus, Nipah virus, Norwalk virus, O'nyong-nyong virus, Orf virus, Oropouche virus, Pichinde virus, Poliovirus, Punta toro phlebovirus, Puumala virus, Rabies virus, Rift valley fever virus, Ross river virus, Rotavirus A, Rotavirus B, Rotavirus C, Rubella virus, Sagiyama virus, Sandfly fever sicilian virus, Sapporo virus, Semliki forest virus, Seoul virus, Sindbis virus, Southampton virus, St. louis encephalitis virus, Tick-borne powassan virus, Toscana virus, Uukuniemi virus, Varicella-zoster virus, Variola virus, Venezuelan equine encephalitis virus, Vesicular stomatitis virus, Western equine encephalitis virus, West Nile virus and Yellow fever virus. In some preferred embodiments, the virus is a coronavirus (e.g. Covid-19 (SARS-CoV2)).

In some embodiments, the infectious agent may be a bacterium selected from any of the genus *Achromobacter, Acinetobacter, Actinobacillus, Aeromonas, Agrobacterium, Alcaligenes, Alteromonas, Bacillus, Bacteroides, Bartonella, Borrelia, Bordetella, Brucella, Burkholderia, Campylobacter, Cardiobacterium, Chlamydia, Chlamydophila, Chromobacterium, Chyseobacterium, Chryseomonas, Citrobacter, Clostridium, Comamonas, Corynebacterium, Coxiella, Cryptobacterium, Edwardsiella, Eikenella, Enterobacter, Enterococcus, Erwinia, Helicobacter, Kingella, Klebsiella, Lactobacillus, Lactococcus, Legionella, Leptospira, Leptotrichia, Leuconostoc, Listeria, Listonella, Mobiluncus, Moraxella, Morganella, Mycobacterium, Mycoplasma, Neisseria, Nocardia, Nocardiopsis, Pantoea, Parachlamydia, Pasteurella, Peptococcus, Peptostreptococcus, Prevotella, Propionibacterium, Proteus, Providencia, Pseudomonas, Ralstonia, Rickettsia, Salmonella, Shewenella, Shigella, Sphingobacterium, Sphingomonas, Staphylococcus, Stenotrophomonas, Streptobacillus, Streptococcus, Streptomyces, Treponem* and *Yersinia,* such as *Acinetobacter, Bacillus, Burkholderia, Chlamydia, Clostridium, Helicobacter, Staphylococcus, Streptococcus, Pseudomonas, Legionella, Listeria, Mycobacterium, Proteus, Klebsiella, Fusobacterium* or other enteric or coliform bacteria.

Thus, for instance, the infectious agent may be a gram-positive bacteria such as, *M. tuberculosis, M. bovis, M. typhimurium, M. bovis* strain BCG, BCG substrains, *M. avium, M. intracellulare, M. africanum, M. kansasii, M. marinum, M. ulcerans, M. avium* subspecies *paratuberculosis, Staphylococcus aureus, Staphylococcus epidermidis, Staphylococcus equi, Streptococcus pyogenes, Streptococcus agalactiae, Listeria monocytogenes, Listeria ivanovii, Bacillus anthracis, B. subtilis, Nocardia asteroides, Actinomyces israelii, Propionibacterium acnes,* and *Enterococcus* species.

In other embodiments, the infectious agent may be caused by a gram-negative bacteria such as *Clostridium tetani, Clostridium perfringens, Clostridium botulinum, Pseudomonas aeruginosa, Vibrio cholerae, Actinobacillus pleuropneumoniae, Pasteurella haemolytica, Pasteurella multocida, Legionella pneumophila, Salmonella typhi, Brucella abortus, Chlamydi trachomatis, Chlamydia psittaci, Coxiella burnetti, Escherichia coli, Neiserria meningitidis, Neiserria gonorrhea, Haemophilus influenzae, Haemophilus ducreyi, Yersinia pestis, Yersinia enterolitica, Escherichia coli, E. hirae, Burkholderia cepacia, Burkholderia pseudomallei, Francisella tularensis, Bacteroides fragilis, Fusobascterium nucleatum,* and *Cowdria ruminantium.*

In some embodiments, the infectious agent may be a fungus, which may be a mould or yeast, preferably a yeast. In some embodiments, the fungus may be selected from any one or more of a Dermatophyte, *Aspergillus* sp. (such as *Aspergillus fumigatus, Aspergillus nigricans* or *flavescens*), *Zygomycota* sp., *Fusarium* sp., *Trichophyton* sp., *Basidiobolus ranarum, Piedraia* sp. (such as *Piedraia hortae*), *Blastomyces dermatitidis, Candida* sp. (such as *Candida albicans*), *Chrysosporium, Coccidioides* sp. (such as *Coccidioides immitis* and *Coccidioides posadasii*), *Conidiobolus* sp. (such as *Conidiobolus coronatus* and *Conidiobolus incongruus*), *Cryptococcus* sp. (such as *Cryptococcus gattii* and *Cryptococcus neoformans*), *Histoplasma* sp. (such as *Histoplasma farciminosum* and *Histoplasma capsula-*

*tum*), *Exserohilum rostratum, Cladosporium* sp., *Saccharomyces* sp., *Lacazia loboi, Paracoccidioides brasiliensis, Penicillium marneffei, Pneumocystis jirovecii, Sporothrix schenckii, Diheterospora zeaspora, Absidia corymbifera, Apophysomyces elegans, Mucor indicus, Rhizomucor pusillus, Rhizopus oryzae, Cunninghamella bertholletiae, Cokeromyces recurvatus, Saksenaea vasiformis, Syncephalastrum racemosum, Conidiobolus* sp. (such as *Conidiobolus coronatus* and *Conidiobolus incongruus*).

In some embodiments, the fungus may be selected from the genera *Candida, Aspergillus, Pneumocystis, Penicillium* and *Fusarium*. Representative fungal species include, but are not limited to, *Candida albicans, Candida dubliniensis, Cryptococcus neoformans, Histoplama capsulatum, Aspergillus fumigatus, Coccidiodes immitis, Paracoccidioides brasiliensis, Blastomyces dermitidis, Pneomocystis carnii, Penicillium marneffi* and *Alternaria* alternate etc. In some embodiments, the infectious agent may be a parasite including *Plasmodium* sp., such as *Plasmodium falciparum, Plasmodium knowlesi, Plasmodium vivax, Plasmodium berghei* and *Plasmodium yoelii* infections, protozoa such as *Toxoplasma* species e.g. *Toxoplasma gondii, Trypanosoma brucei, Trypanosoma cruzi, Leishmania* species such as *Leishmania major, Schistosoma* such as *Schistosoma mansoni* and *Entamoeba histolytica*.

The nucleic acids obtained from the method may be analysed, e.g. to detect an infectious agent as described above. The step of analysing the nucleic acids may use any nucleic acid analysis. For instance, the nucleic acids may be analysed to determine their sequence (e.g. by nucleic acid sequencing), although actual sequence determination may not be required—any method of analysing the sequence may be used.

The step of analysis may identify (detect) one or more nucleic acids obtained from biological material. Hence the analysis step may include or use any method which identifies the "target" nucleic acid, e.g. the nucleic acid from the infectious agent, e.g. virus. Generally such a method will be a sequence-specific method. For example, the method may use sequence-specific primers or probes for a specific nucleic acid molecule to be detected or analysed, e.g. a DNA molecule corresponding to a nucleic acid, e.g. RNA or cDNA, that is indicative to a particular infectious agent. Typically in such a method sequence-specific amplification primers, e.g. PCR primers may be used.

Thus in one embodiment, amplification-based, especially PCR-based methods of sequence analysis are used. In some embodiments, quantitative PCR (qPCR) is used. In some embodiments, the PCR may be a reverse transcription PCR (RT-PCR). In some embodiments, the PCR may be a real-time PCR.

Sequence analysis of the nucleic acids may be direct or indirect. Thus, the sequence analysis substrate (which may be viewed as the molecule which is subjected to the sequence analysis step or process) may directly be the isolated nucleic acid or it may be a molecule which is derived therefrom. Thus, for example, in the context of sequence analysis step which involves a sequencing reaction, the sequencing template may be the isolated nucleic acid or it may be a molecule derived therefrom. For example, a DNA molecule may be directly subjected to sequence analysis (e.g. sequencing), i.e. may directly take part in the sequence analysis reaction or process (e.g. the sequencing reaction or sequencing process, or be the molecule which is sequenced or otherwise identified). Alternatively, the nucleic acid may be subjected to a step of reverse transcription and optionally second strand synthesis and/or amplification before sequence analysis (e.g. sequencing or identification by other means). The sequence analysis substrate (e.g. template) may thus be an amplicon or a first or second strand of a reverse transcription reaction from an isolated nucleic acid.

According to the present invention the detection step typically involves an amplification step to generate an amplification product which is detected, typically by amplification of a portion of a target nucleic acid.

The target nucleic acid may be detected using any convenient protocol. The particular detection protocol may vary depending on the sensitivity desired and the application in which the method is being practiced. In the method of the invention as described herein, the detection protocol may include an amplification component, in which the copy number of the target nucleic acid (or part thereof) is increased, e.g., to enhance sensitivity of the particular assay. However, it is possible that in other methods the target nucleic acid may be directly detected without any amplification.

Although not a preferred embodiment of the method of the invention, where detection without amplification is practicable, the target nucleic acid may be detected in a number of different ways. For example, the target nucleic acid may be directly labelled, e.g., fluorescently, or otherwise spectrophotometrically, or radioisotopically labelled or with any signal-giving label, such that the target nucleic acid is directly labelled. In these embodiments, the directly labelled target nucleic acid may be separated from the remainder of the isolated nucleic acids, in order to detect the target nucleic acid. Alternatively, conformationally selective probes, e.g., molecular beacons may be employed to detect to the presence of the target nucleic acid, where these probes are directed to a sequence that is only present in the target nucleic acid.

In a preferred embodiment of the subject methods, the analysis and detection step includes an amplification step, where the copy number of target nucleic acid or part thereof is increased, e.g., in order to enhance sensitivity of the assay. The amplification may be linear or exponential, as desired, where representative amplification protocols of interest include, but are not limited to: polymerase chain reaction (PCR); isothermal amplification, Rolling circle amplification, etc. In a particularly preferred embodiment of the invention, the amplification protocol is quantitative-PCR (qPCR) or real-time PCR. As noted above, where the target nucleic acid is an RNA molecule, the amplification step may first require a step of reverse transcription to generate a DNA copy (cDNA) of the target nucleic acid for amplification.

Rolling circle amplification using padlock probes, e.g. as described in U.S. Pat. No. 6,558,928, or indeed any circular nucleic acid molecule as a template can also be useful in amplifying an existing "signal" nucleic acid molecule or part thereof, e.g. an target nucleic acid obtained from a biological sample. Thus, in some embodiments, the target nucleic acid (or part thereof) may be amplified by rolling circle amplification. In one embodiment, RCA is performed using padlock probes. In another embodiment, RCA is performed using circular templates (circular oligonucleotides).

Where the detection step includes an amplification step (more specifically a step of in vitro amplification of the target nucleic acid or part thereof), the amplified product (or amplification product) may be detected, to detect the target nucleic acid.

In a particularly preferred embodiment of the invention the target nucleic acid is amplified by PCR, wherein the PCR is quantitative PCR and the amplified nucleic acid molecules are quantified using an intercalating dye.

Representative detectable molecules that find use in such embodiments include fluorescent nucleic acid stains, such as phenanthridinium dyes, including monomers or homo- or heterodimers thereof, that give an enhanced fluorescence when complexed with nucleic acids. Examples of phenanthridinium dyes include ethidium homodimer, ethidium bromide, propidium iodide, and other alkyl-substituted phenanthridinium dyes. In another embodiment of the invention, the nucleic acid stain is or incorporates an acridine dye, or a homo- or heterodimer thereof, such as acridine orange, acridine homodimer, ethidium-acridine heterodimer, or 9-amino-6-chloro-2-methoxyacridine. In yet another embodiment of the invention, the nucleic acid stain is an indole or imidazole dye, such as Hoechst 33258, Hoechst 33342, Hoechst 34580 (BIOPROBES 34, Molecular Probes, Inc. Eugene, Oreg., (May 2000)) DAPI (4',6-diamidino-2-phenylindole) or DIPI (4',6-(diimidazolin-2-yl)-2-phenylindole). Other permitted nucleic acid stains include, but are not limited to, 7-aminoactinomycin D, hydroxystilbamidine, LDS 751, selected psoralens (furocoumarins), styryl dyes, metal complexes such as ruthenium complexes, and transition metal complexes (incorporating $Tb^{3+}$ and $Eu^{3+}$, for example). In certain embodiments of the invention, the nucleic acid stain is a cyanine dye or a homo- or heterodimer of a cyanine dye that gives an enhanced fluorescence when associated with nucleic acids. Any of the dyes described in U.S. Pat. No. 4,883,867 to Lee (1989), U.S. Pat. No. 5,582,977 to Yue et al. (1996), U.S. Pat. No. 5,321,130 to Yue et al. (1994), and U.S. Pat. No. 5,410,030 to Yue et al. (1995) (all four patents incorporated by reference) may be used, including nucleic acid stains commercially available under the trademarks TOTO, BOBO, POPO, YOYO, TO-PRO, BO-PRO, PO-PRO and YO-PRO from Molecular Probes, Inc., Eugene, Oreg. Any of the dyes described in U.S. Pat. No. 5,436,134 to Haugland et al. (1995), U.S. Pat. No. 5,658,751 to Yue et al. (1997), and U.S. Pat. No. 5,863,753 to Haugland et al. (1999) (all three patents incorporated by reference) may be used, including nucleic acid stains commercially available under the trademarks SYBR Green, SYTO, SYTOX, PICOGREEN, OLIGREEN, and RIBOGREEN from Molecular Probes, Inc., Eugene, Oreg. In yet other embodiments of the invention, the nucleic acid stain is a monomeric, homodimeric or heterodimeric cyanine dye that incorporates an aza- or polyazabenzazolium heterocycle, such as an azabenzoxazole, azabenzimidazole, or azabenzothiazole, that gives an enhanced fluorescence when associated with nucleic acids, including nucleic acid stains commercially available under the trademarks SYTO, SYTOX, JOJO, JO-PRO, LOLO, LO-PRO from Molecular Probes, Inc., Eugene, Oreg. A further intercalating dye that may be of use in the methods of the invention is EvaGreen™ from Biotium Inc.

In yet other embodiments, a signal producing system that is specific for the amplification product, as opposed to double stranded molecules in general, may be employed to detect the amplification product. In these embodiments, the signal producing system may include a probe nucleic acid that specifically binds to a sequence found in the amplification product, where the probe nucleic acid may be labelled with a directly or indirectly detectable label. A directly detectable label is one that can be directly detected without the use of additional reagents, while an indirectly detectable label is one that is detectable by employing one or more additional reagents, e.g., where the label is a member of a signal producing system made up of two or more components. In many embodiments, the label is a directly detectable label, where directly detectable labels of interest include, but are not limited to: fluorescent labels, radioisotopic labels, chemiluminescent labels, and the like. In many embodiments, the label is a fluorescent label, where the labelling reagent employed in such embodiments is a fluorescently tagged nucleotide(s), e.g. fluorescently tagged CTP (such as Cy3-CTP, Cy5-CTP) etc. Fluorescent moieties which may be used to tag nucleotides for producing labelled probe nucleic acids include, but are not limited to: fluorescein, the cyanine dyes, such as Cy3, Cy5, Alexa 555, Bodipy 630/650, and the like. Other labels, such as those described above, may also be employed as are known in the art.

The next step in the subject methods is signal detection from the labelled amplification products of interest (e.g. labelled target nucleic acids), where signal detection may vary depending on the particular signal producing system employed. In certain embodiments, merely the presence or absence of detectable signal, e.g., fluorescence, is determined and used in the subject assays, e.g., to determine or identify the presence or absence of the target nucleic acid (and therefore the infectious agent). Depending on the particular label employed, detection of a signal may indicate the presence or absence of the target nucleic acid.

In those embodiments where the signal producing system is a fluorescent signal producing system, signal detection typically includes detecting a change in a fluorescent signal from the reaction mixture to obtain an assay result. In other words, any modulation in the fluorescent signal generated by the reaction mixture is assessed. The change may be an increase or decrease in fluorescence, depending on the nature of the label employed, but in certain embodiments is an increase in fluorescence. The sample may be screened for an increase in fluorescence using any convenient means, e.g., a suitable fluorimeter, such as a thermostable-cuvette or plate-reader fluorimeter. Fluorescence is suitably monitored using a known fluorimeter. The signals from these devices, for instance in the form of photo-multiplier voltages, are sent to a data processor board and converted into a spectrum associated with each sample tube. Multiple tubes, for example 96 tubes, can be assessed at the same time.

Where the detection protocol is a real time protocol, e.g., as employed in real time PCR reaction protocols, data may be collected in this way at frequent intervals, for example once every 3 minutes, throughout the reaction. By monitoring the fluorescence of the reactive molecule from the sample during each cycle, the progress of the amplification reaction can be monitored in various ways. For example, the data provided by melting peaks can be analyzed, for example by calculating the area under the melting peaks and these data plotted against the number of cycles. In a preferred embodiment of the invention, the fluorescence signal is achieved using a dye that intercalates in double stranded nucleic acid molecules.

The spectra generated in this way can be resolved, for example, using "fits" of pre-selected fluorescent moieties such as dyes, to form peaks representative of each signalling moiety (i.e. fluorophore). The areas under the peaks can be determined which represents the intensity value for each signal, and if required, expressed as quotients of each other. The differential of signal intensities and/or ratios will allow changes in labelled probes to be recorded through the reaction or at different reaction conditions, such as temperatures. The changes are related to the binding phenomenon between the oligonucleotide probe and the target sequence or degradation of the oligonucleotide probe bound to the target sequence. The integral of the area under the differential peaks will allow intensity values for the label effects to be calculated.

Screening the mixture for a change in fluorescence provides one or more assay results, depending on whether the sample is screened once at the end of the primer extension reaction, or multiple times, e.g., after each cycle, of an amplification reaction (e.g., as is done in real time PCR monitoring).

The data generated as described above can be interpreted in various ways. In its simplest form, an increase or decrease in fluorescence from the sample in the course of or at the end of the amplification reaction is indicative of an increase in the amount of the target nucleic present in the sample, e.g., as correlated to the amount of amplification product detected in the reaction mixture, suggestive of the fact that the amplification reaction has proceeded and therefore the target nucleic acid was in fact present in the initial biological sample. Quantification is also possible by monitoring the amplification reaction throughout the amplification process. Quantification may also include assaying for one or more nucleic acid controls in the reaction mixture.

In this manner, isolated nucleic acids obtained from the method may readily be screened (or assessed or assayed etc.) for the presence of target nucleic acids, e.g. nucleic acids indicative of the presence of infectious agents. The methods are suitable for detection of a single target nucleic acid as well as multiplex analyses, in which two or more different target nucleic acids are assayed in the sample. In these latter multiplex situations, the number of different sets of probes that may be employed typically ranges from about 2 to about 20 or higher, e.g., as up to 100 or higher, 1000 or higher, etc.

The target nucleic acid may be detected directly or preferably after amplification using any of the well-established methods for analysis of nucleic acid molecules known from the literature including liquid chromatography, electrophoresis, mass spectrometry, microscopy, real-time PCR (quantitative PCR), fluorescent probes etc. A preferred embodiment of the method of the invention utilises quantitative or real-time PCR, wherein the PCR may be a reverse transcription PCR (i.e. for the detection of a target RNA, e.g. viral RNA). Of particular interest is the combination of the present method with a "DNA array" read-out format. Several unique target nucleic acids may be hybridized to a standardized DNA array carrying a number of oligonucleotide sequences (tags) complementary to the target nucleic acid sequences. Each target nucleic acid hybridized to the array may be identified by its location on the DNA array and the detected intensity in a given hybridization spot will be indicative of the quantity of that specific target nucleic acid. Detection of the target nucleic acid may be accomplished by spectrometry, fluorescence, radioisotopes etc. Fluorescent moieties may conveniently be introduced into the extension products using fluorescently labelled primers or fluorescently labelled nucleotides in the amplification reaction (PCR). The DNA array may be a simple dot-blot array on a membrane containing a small number of spots or a high density array carrying hundreds of thousands of spots.

In a further embodiment, the invention provides a kit, e.g. for use in a method of isolating nucleic acids from a sample comprising biological material, comprising:

(a) a lysis solution as defined herein; and (b) silica-coated magnetic particles, e.g. as defined herein.

In some embodiments, the kit may further comprise an elution buffer as defined herein.

In some embodiments, the kit may further comprise means for amplifying and/or detecting a target nucleic acid that may be isolated from a biological sample. For instance, the target nucleic acid may be a nucleic acid from an infectious agent. The amplification and detection means may comprise fluorescently labelled nucleotides or oligonucleotides or intercalating dyes (e.g. SYBR Green® and/or EvaGreen™), single strand binding proteins, and PCR amplification reagents (e.g., nucleotides, buffers, cations, etc.), and the like, and/or one or more oligonucleotide primers for use in an amplification reaction, e.g. a real-time PCR, qPCR, reverse transcription PCR (e.g. RT-qPCR) as described above.

The invention will be further described with reference to the following non-limiting Examples with reference to the following drawings in which:

FIG. 1 shows the silica coated magnetic particles of MB1.

EXAMPLES

Example 1—Synthesis of Iron Oxide Nanoparticles (IONP)

8.0 g of $FeCl_2 \cdot 4H_2O$ and 21.6 μm of $FeCl_3 \cdot 6H_2O$ were weighed into separate 100 ml volumetric flasks and each flask filled to 100 ml with MQ-water. 84.6 g MQ water was placed in a beaker and 15.4 ml of 25 wt % $NH_4OH$ was added. 10 ml of iron chloride stock solution was added to the $NH_4OH$/water dropwise using a burette under vigorous stirring (4-500 rpm) to create a suspension.

40 mL of the suspension was transferred to a 40 mL centrifuge tube, and the magnetically formed particles were separated and the supernatant discarded. The rest of the suspension was added to the particles and the separation process repeated until all the slurry is separated.

The separated particles are washed thrice with MQ-water and suspended in 15 mL MQ-water resulting in the final volume of 20 mL. The particle weight is adjusted to 50 mg/ml.

Example 2—Iron Oxide Magnetic Nanoparticles—Small Scale 2 ml of TEOS was mixed with 20 ml of ethanol in a vial and kept stirring at 500 rpm for 15 minutes. 1 ml of IONP (~50 mg) aq. dispersion from example 1 was first magnetically separated from the water and cleaned thrice with ethanol. The washed IONPs were added into the reaction mixture and stirred for 30 minutes.

4 ml of MQ water followed by 5 ml of 25 wt % $NH_4OH$ was added to the reaction mixture and stirred for 30 minutes. The reaction mixture was heated to 82° C. over 15 minutes and the reaction left running overnight (at least 12 hours). The ratio of ethanol to added water is approx 5:1 (and to total water is 2.6:1)

The reaction mixed was cooled to room temperature and the formed silica coated IONPs magnetically separated. These were washed two times with ethanol and seven times with MQ water. The washed silica coated IONPs were finally re-dispersed in 25 ml MQ water. This sample is called MB1. The concentration of silica coated IONPs in water for the small scale batch is 6-7 mg/ml.

Example 3—Scaled Up Synthesis of Silica Coated IONPS (Magnetic Beads)

20 ml of TEOS was mixed with 380 ml of ethanol in a water jacketed reactor and kept stirring at 500 rpm for 15 minutes. 10 ml of IONP (~500 mg) dispersion from example 1 was first magnetically separated from the water and cleaned thrice with Ethanol. The particles are redispersed in 20 ml of ethanol and the dispersion added into the reaction mixture and stirred for 30 minutes.

40 ml of MQ water followed by 5 ml of 25 wt % $NH_4OH$ was added to the reaction mixture and stirred for 30 minutes. The reaction mixture was heated to 82° C. over 15 minutes and the reaction left running overnight (at least 12 hours). The ratio of ethanol to added water is approx. 10:1 (and to total water 9.1:1)

The reaction mixed was cooled to room temperature and the formed silica coated IONPs magnetically separated. These were washed two times with ethanol and seven times with MQ water. The washed silica coated IONPs were finally re-dispersed in 250 ml MQ water. This sample is called MB2. The concentration for the scaled up batch is between 9-10 mg/ml.

Properties of the Silica Coated IONPs

The pH of MB1 and MB2 was measured. The pH was 9.3 for MB1 and 9.1 for MB2. PDI was measured as 0.0014 and 0.0013 for MB1 and MB2 respectively.

The zeta potential of MB1 and MB2 was measured using a Malvern NanoSizer. The zeta potential was −52 mV for MB1 and −62 mV for MB2.

SEM Analysis

Sample Preparation

Bead suspension is prepared at a concentration of approximately 0.1 to 0.01 percent by volume, and dispersion is ensured by vortexing or ultrasonicating the diluted sample. A flat, conductive substrate is prepared. Clean Si wafer pieces or mica with a conductive coating—e.g. thick gold coating—are ideal. The conductive sample is plasma cleaned using $O_2$ plasma for a time of 1 minute, increasing hydrophilicity.

Apply 50 µL of dilute bead suspension to the freshly plasma treated substrate, and dry at room temperature or elevated temperature until bone dry. Samples are affixed to a SEM stub using conductive adhesive, and electric contact from sample to stub is confirmed.

Imaging

A SEM capable of high resolution needs to be utilized, e.g. a Field-Effect gun SEM (FE-SEM/FEG-SEM). Samples are introduced to the microscope, and imaged at an adequate resolution, e.g. 5-20 k. Several images must be taken of different areas on each sample, totalling a number of identifiable beads, approaching 100, at different positions on the sample surface. These micrographs are ideally, for automation purposes, recorded at the same resolution. Where possible, a detector or detector combination with low topographic contrast is desirable.

Image Analysis

Visual inspection is the initial inspection of the samples, samples exhibiting obvious deviation from the desired particle shape, size and uniformity of either can be rejected at this point. After an initial visual inspection, images can be analyzed and beads measured manually. More optimally they are run through an algorithm which thresholds the image, producing a binary mask separating the particles and the background by contrast. After thresholding the image is analyzed counting the particles per unit area, measuring their size and shape descriptors, e.g. circularity, aspect ratio, Feret's diameter, etcetera are measured and exported for statistical analysis. Each sample is then analyzed using appropriate computer software for this purpose, returning size and shape descriptor distributions, and relevant statistics to the operator.

For both the batches, MB1 and MB2, mean particle diameters are found to be 0.41 and 0.45 µm respectively. Beads in both batches were very monodisperse (CV=4%). The particles of MB1 are shown in FIG. 1.

Example 4—Large Scale Synthesis of Silica Coated IONPS (Magnetic Beads)

48 ml of TEOS was added to 700 ml of ethanol in a vial and stirred at 500 rpm for 15 minutes. ~20 ml of IONP (1200 mg) dispersion from example 1 was first magnetically separated from the water and cleaned thrice with Ethanol. The washed IONPs were redispersed in 260 mL ethanol and added into the reaction mixture. The reaction mixture was stirred for 30 minutes and 200 ml of MQ water was then added followed by 50 ml of 25 wt % $NH_4OH$ and stirred for 30 minutes. The mixture was heated to 82° C. over 15 minutes and left overnight (at least 12 hours). The ratio of ethanol to added water is approx. 4.8:1 (and to total water 4:1).

The reaction mixed was cooled to room temperature and the formed silica coated IONPs magnetically separated. These were washed two times with ethanol and seven times with MQ water. The washed silica coated IONPs were finally re-dispersed in 200 ml MQ water. This sample is called MBL (Magnetic Beads Large Scale).

The concentration for the scaled up batch is between 26.3 mg/ml.

The pH of Magnetic Beads Large Scale was measured. The pH was 9.5.

Example 5—Large Scale Synthesis of Silica Coated IONPS (Magnetic Beads) at Room Temperature 48 ml of TEOS was added to 700 ml of isopropanol in a vial and stirred at 500 rpm for 15 minutes. ~20 ml of IONP (1200 mg) dispersion from example 1 was first magnetically separated from the water and cleaned thrice with isopropanol. The washed IONPs were redispersed in 260 mL isopropanol and added into the reaction mixture. The reaction mixture was stirred for 30 minutes and 200 ml of MQ water was then added followed by 50 ml of 25 wt % $NH_4OH$ and stirred for 30 minutes. The mixture was left overnight (at least 12 hours). The ratio of ethanol to added water is approx. 4.8:1 (and to total water 4:1).

The formed silica coated IONPs are magnetically separated. These were washed two times with isopropanol and seven times with MQ water. The washed silica coated IONPs were finally re-dispersed in 200 ml MQ water. This sample is called MBL (Magnetic Beads Large Scale).

The concentration for the scaled up batch is between 29.3 mg/ml.

The pH of Magnetic Beads Large Scale was measured. The pH was 10.2.

Example 6—Method for Nucleic Acid Extraction from a Biological Sample Using Silica-Coated Magnetic Particles A lysis solution was prepared according to Table 1. A suspension of silica-coated magnetic particles (prepared using the method described in Example 3) was prepared according to Table 2 (magnetic particle mix). An elution buffer was prepared according to Table 3.

TABLE 1

| | Final concentration | to 100 ml (for 5*96 Wplates) |
|---|---|---|
| Guanidine thiocyanate | 4M | 47.3 g |
| Tri-HCl pH-7.8 | 50 mM | 5 ml of 1M stock |
| N-lauroyl Sarcosine | 2% | 2 g |
| EDTA | 20 mM | 4 ml of 0.5M stock |
| Glycogen | 1 mg/ml | 500 ul of 200 mg/ml stock |
| TCEP | 10 mM | |

TABLE 2

| | Per sample | For 100 samples |
|---|---|---|
| Isopropanol | 400 µl | 40 ml |
| Proteinase K | 100 µg/ml | 700 µl of 10 mg/ml stock |
| Magnetic Particles | 20 µl of a suspension comprising about 10 mg/ml | 2 ml |

TABLE 3

| | Per sample | For 100 samples |
|---|---|---|
| Nuclease free water | 50 µl | 5 ml |
| Tween 20 | 1% | 250 ul of 20% stock |

Protocol

1. Pipette out 200 µl Lysis solution (per sample tube or per well if using plate, e.g. 96 well plate)
2. Add 100 µl sample (i.e. comprising biological material), mix (pipetting/vortexing)
3. Resuspend magnetic particle-mix. Vortex thoroughly to resuspend all particles
4. Add 400 µl particle-mix to each sample/lysis tube, mix (pipetting/vortexing)
5. Keep the particles in solution for 10 minutes by mixing/shaking
6. Remove supernatant using a magnet
7. Wash the particles in 400 µl isopropanol, mix for 2 minutes
8. Remove supernatant using a magnet
9. Wash the particles in 400 µl 80% EtOH, mix for 2 minutes
10. Remove supernatant using a magnet
11. Wash the particles in 400 µl 80% EtOH, mix for 2 minutes
12. Remove supernatant using a magnet
13. Dry the particles for 10 minutes at room temperature
14. Resuspend the particles in 50 µl elution buffer, mix for 5 minutes
15. Collect the supernatant for qPCR.

Set-Up for KingFisher Robot:

| Position | Plate type | Content | Volume |
|---|---|---|---|
| 1 | KF 96 deep-well | Lysate (Lysis buffer, sample, bead mix) | 700 ul |
| 2 | KF 96 deep-well | Isopropanol wash | 400 ul |
| 3 | KF 96 deep-well | 80% Ethanol wash | 400 ul |
| 4 | KF 96 deep-well | 80% Ethanol wash | 400 ul |

-continued

| Position | Plate type | Content | Volume |
|---|---|---|---|
| 5 | KF 96 standard | Elution buffer | 50 ul |
| 6 | KF 96 standard | 96 tip comb for deep-well maqnets | |

Protocol

1. Transfer 200 µl Lysis buffer to each well
2. Add 100 ul Sample to Lysis Buffer, leave at RT for minimum 5 minutes
3. Add 400 ul Bead-mix
4. Prepare reagents in plates according to table.
5. Start program on instrument
6. After run, collect eluted sample in Plate 6 to PCR.

Example 7—Comparison of Methods for Detection of Covid-19 Virus from Viscous Expectorate Samples Nucleic acid was isolated from viscous expectorate samples from patients suspected of being infected with the covid-19 virus (a coronavirus) using the protocol described in Example 6 and a commercial nucleic acid extraction kit, NucliSENS® EASYMAG® (bioMerieux), which also uses silica-coated magnetic particles. The protocol described in Example 6 used 100 µl of patient sample, whereas 200 µl was used as the input for the commercial kit. Nucleic acid obtained from each sample was used in a standard reverse transcription qPCR (RT-qPCR) to detect covid-19 target nucleic acids.

Table 4 below shows the cycle threshold (Ct) values from the RT-qPCR and the results demonstrate that the Ct values are lower for almost all patient samples, indicating that the nucleic acid isolated using the protocol in Example 6 results in a more sensitive assay. It was determined that the isolation protocol of Example 6 results in the isolation of about 3 times more RNA compared to the commercial kit. This facilitates the detection of nucleic acids that are present in a biological sample at very low levels.

Samples from subjects not infected with the covid-19 virus yielded negative results, as expected.

TABLE 4

| Samples | Ct-values NucliSENS ® kit | Ct-values Example 3 protocol | Parallel sample from Example 3 protocol |
|---|---|---|---|
| 2 | 18.89 | 18.34 | |
| 3 | 19.24 | 20.58 | |
| 4 | 18.12 | 18.81 | |
| 5 | 14.45 | 13.13 | |
| 6 | 29.35 | 26.89 | |
| 7 | 33.07 | 32.64 | 31.21 |
| 8 | 23.13 | 22.56 | |
| 9 | 35.11 | 36.73 | |
| 10 | 21.7 | 19.28 | |
| 11 | 28.46 | 28.06 | |
| 12 | 24.51 | 24.93 | |
| 13 | 31.65 | 31.77 | 32.78 |
| 14 | 25.39 | 24.97 | |
| 15 | 16.51 | 15.25 | |
| 16 | 34.71 | 34.41 | 33.89 |
| 17 | 30.37 | 29.27 | 30.31 |
| 18 | 26.02 | 24.71 | |
| 19 | 31.27 | 30.14 | 29.32 |
| 20 | 18.99 | 17.8 | |
| 21 | 25.85 | 24.62 | |
| 22 | 17.15 | 16.82 | |
| 23 | 29.16 | 27.22 | |

TABLE 4-continued

| Samples | Ct-values NucliSENS ® kit | Ct-values Example 3 protocol | Parallel sample from Example 3 protocol |
|---|---|---|---|
| 24 | 31.98 | 29.12 | 30.26 |
| 25 | 32.77 | 32.03 | 30.89 |

Example 8—Effects of Various Components in the Isolation Protocol

The effects of various components used in the nucleic acid protocol described in Example 6 were assessed using a viscous expectorate sample from a Covid-19 positive patient. The nucleic acids obtained from each variant isolation method from the sample were used in a standard qPCR to detect covid-19 target nucleic acids.

Variations of the protocol described in Example 6 as outlined in Table 5. For instance, the elution step was performed with and without Tween. The reducing agent in the lysis buffer was changed, i.e. from TCEP to DTT. Also, in some cases, proteinase K was added to the lysis solution after contact with the expectorate sample but before the addition of the particle mix (without proteinase K)—see "Proteinase K in Lysis buffer".

TABLE 5

| Well | Parameters | Cq |
|---|---|---|
| A01 | Standard setup | Undetermind |
| B01 | Standard setup | Undetermind |
| C01 | Standard setup 1% Tween in elution buffer | 35.74 |
| D01 | Standard-setup 1% Tween in elution buffer | 35.05 |
| A02 | 10 mM TCEP in Lysis Buffer | 28.33 |
| B02 | 10 mM TCEP in Lysis Buffer | 28.35 |
| C02 | 10 mM TCEP in Lysis Buffer 1% Tween in elution buffer | 28.22 |
| D02 | 10 mM TCEP in Lysis Buffer 1% Tween in elution buffer | 27.68 |
| E02 | 20 ug Proteinase K in Lysis Buffer | 34.46 |
| F02 | 20 ug Proteinase K in Lysis Buffer | 32.45 |
| G02 | 20 ug Proteinase K in Lysis Buffer 1% Tween in elution buffer | 34.48 |
| H02 | 20 ug Proteinase K in Lysis Buffer 1% Tween in elution buffer | 30.14 |
| A03 | 200 ug Proteinase K in Lysis Buffer | 29.06 |
| B03 | 200 ug Proteinase K in Lysis Buffer | 28.10 |
| C03 | 200 ug Proteinase K in Lysis Buffer 1% Tween in elution buffer | 28.15 |
| D03 | 200 ug Proteinase K in Lysis Buffer 1% Tween in elution buffer | 28.10 |
| E01 | 80 mM DTT in Lysis Buffer | 29.89 |
| F01 | 80 mM DTT in Lysis Buffer | 29.54 |
| G01 | 80 mM DTT in Lysis Buffer 1% Tween in elution buffer | 29.40 |
| H01 | 80 mM DTT in Lysis Buffer 1% Tween in elution buffer | 29.49 |
| E03 | Pos CTRL | 31.53 |
| F03 | Neg CTRL | |

The results demonstrate that the use of TCEP significantly enhances the detection of covid-19 nucleic acid. Similarly, the use of high amounts of proteinase K during the lysis step also improves detection of covid-19 nucleic acid.

Example 9—Formulation for Alternative Lysis Solutions

An alternative lysis solution for use in the protocol described in Example 6 may be prepared according to the formulation in Table 6.

TABLE 6

| | Final concentration | to 1000 ml |
|---|---|---|
| Guanidine thiocyanate | 4M | 473 g |
| Tri-HCl pH-7.8 | 50 mM | 50 ml of 1M stock |
| Triton X-100 | 1.20% | 12 g |
| EDTA (pH 7.8) | 20 mM | 40 ml of 0.5M stock |
| Glycogen | 1 mg/ml | 1.0 g |

A further alternative lysis solution can be prepared by omitting the glycogen component from the formulation in Table 6.

The invention claimed is:

1. A process for the preparation of a silica coated magnetic particles comprising
   (I) combining magnetic particles and an alkoxysilane in a C1-4-alcohol in the absence of water to form a mixture;
   (II) adding water and a hydroxide to the mixture of step (I) such that the weight ratio of C1-4-alcohol to water in the mixture is 1:1 to 15:1 and heating the resulting mixture to a temperature in the range of 15 to 90° C. in order to form silica coated magnetic particles;
   (III) washing the silica coated magnetic particles of step (II) with water and/or alcohol solvent, until the pH of the silica coated magnetic particles when suspended in water is between 8 and 11.

2. A process as claimed in claim 1, wherein the C1-4-alcohol is ethanol or isopropanol.

3. A process as claimed in claim 1, wherein the weight ratio of C1-4-alcohol to water in the resulting mixture of step (II) is 3:1 to 12:1.

4. A process as claimed in claim 1, wherein the particles are iron oxide nanoparticles.

5. A process as claimed in claim 1, wherein the temperature is 75 to 85° C. or 20 to 30° C.

6. A process as claimed in claim 1, wherein the pH of the silica coated magnetic particles when suspended in water is 9 to 10.

7. A process as claimed in claim 1, wherein the alkoxysilane is tetraorthoethylsilicate.

8. A process as claimed in claim 1, further comprising suspending the silica coated magnetic particles in water wherein the concentration of said particles in water is 5 to 35 mg/ml.

9. A process as claimed in claim 1, further comprising suspending the silica coated magnetic particles wherein the zeta potential of the suspension is −20 to −90 mV.

10. A process as claimed in claim 1, wherein the magnetic particles that are combined with the alkoxysilane in step (I) are coated with an organic polyacid or organic polyacid salt coating.

11. A process as claimed in claim 1, wherein the weight ratio of C1-4-alcohol to water in the resulting mixture of step (II) is 3:2 to 5:1.

12. A process as claimed in claim 1, wherein the magnetic particles that are combined with the alkoxysilane in step (I) are coated with citrate.

* * * * *